US012131731B2

United States Patent
Trehan

(10) Patent No.: US 12,131,731 B2
(45) Date of Patent: Oct. 29, 2024

(54) METHOD AND SYSTEM FOR ANALYSING ACTIVITY PERFORMANCE OF USERS THROUGH SMART MIRROR

(71) Applicant: Rajiv Trehan, Bangkok (TH)

(72) Inventor: Rajiv Trehan, Bangkok (TH)

(73) Assignee: Rajiv Trehan, Bangkok (TH)

( * ) Notice: Subject to any disclaimer, the term of this patent is extended or adjusted under 35 U.S.C. 154(b) by 398 days.

(21) Appl. No.: 17/467,374

(22) Filed: Sep. 6, 2021

(65) Prior Publication Data

US 2022/0072380 A1 Mar. 10, 2022

Related U.S. Application Data

(60) Provisional application No. 63/074,539, filed on Sep. 4, 2020.

(51) Int. Cl.
*G06N 20/00* (2019.01)
*A63B 24/00* (2006.01)
*A63B 71/06* (2006.01)
*G06V 40/20* (2022.01)
(Continued)

(52) U.S. Cl.
CPC .......... *G10L 15/18* (2013.01); *A63B 24/0006* (2013.01); *A63B 24/0062* (2013.01); *A63B 24/0075* (2013.01); *A63B 24/0087* (2013.01); *A63B 71/0622* (2013.01); *G06N 20/00* (2019.01); *G06V 40/23* (2022.01); *G10L 15/22* (2013.01); *A63B 2024/0009* (2013.01); *A63B 2024/0015* (2013.01); *A63B 2024/0071* (2013.01); *A63B 2024/0096* (2013.01);
(Continued)

(58) Field of Classification Search
CPC . A63B 24/00; A63B 24/0006; A63B 71/0622; A63B 2024/0015; A63B 2024/0096; G06N 20/00; G06V 40/23
See application file for complete search history.

(56) References Cited

U.S. PATENT DOCUMENTS

| | | | | |
|---|---|---|---|---|
| 8,328,691 | B2 * | 12/2012 | Lanfermann | A63B 69/00 |
| | | | | 482/901 |
| 10,116,873 | B1 * | 10/2018 | Campbell | G02B 5/08 |
| 10,416,755 | B1 * | 9/2019 | Erivantcev | G06V 10/82 |

(Continued)

FOREIGN PATENT DOCUMENTS

WO WO-2019231982 A1 * 12/2019 ............. A45D 42/00

*Primary Examiner* — Jay Trent Liddle
*Assistant Examiner* — Alyssa N Brandley
(74) *Attorney, Agent, or Firm* — Kendal M. Sheets

(57) ABSTRACT

This disclosure relates to method and system for analyzing activity performance of a user in real-time through a smart mirror. The method includes capturing in real-time multimedia data of current activity performance of the user; processing in real-time the captured multimedia data to determine a set of user performance parameters and an estimated future field of view of the user relative to the smart mirror; generating in real-time a pose skeletal model based on the estimated future field of view and the estimated future pose and motion of the user; augmenting a reflection of the user on the smart mirror with one of the pose skeletal model and the plurality of key points overlayed on top of the reflection; comparing the set of user performance parameters with a set of target activity performance parameters; and generating feedback for the user based on the comparing.

20 Claims, 20 Drawing Sheets

(51) Int. Cl.
*G10L 15/18* (2013.01)
*G10L 15/22* (2006.01)

(52) U.S. Cl.
CPC . *A63B 2071/0627* (2013.01); *A63B 2220/806* (2013.01); *A63B 2225/12* (2013.01)

(56) References Cited

U.S. PATENT DOCUMENTS

| | | | |
|---|---|---|---|
| 2012/0274508 A1* | 11/2012 | Brown | A63B 24/0062 |
| | | | 342/357.57 |
| 2014/0361977 A1* | 12/2014 | Stafford | A63F 13/212 |
| | | | 345/156 |
| 2017/0053456 A1* | 2/2017 | Cho | G06F 1/163 |
| 2017/0358135 A1* | 12/2017 | Trehan | G06Q 30/0623 |
| 2018/0264347 A1* | 9/2018 | Tran | G06V 40/28 |
| 2019/0197850 A1* | 6/2019 | Kristiansen | G08B 13/19652 |
| 2019/0272724 A1* | 9/2019 | Greene | G08B 25/08 |
| 2020/0014967 A1* | 1/2020 | Putnam | H04N 21/41265 |
| 2020/0047055 A1* | 2/2020 | Ward | A63B 21/0058 |
| 2021/0173474 A1* | 6/2021 | Sztuk | G06T 19/006 |
| 2021/0240257 A1* | 8/2021 | Mironov | G06F 3/012 |

* cited by examiner

METHOD AND SYSTEM FOR ANALYSING ACTIVITY PERFORMANCE OF USERS THROUGH SMART MIRROR

CROSS-REFERENCE TO RELATED APPLICATION

This application claims priority benefits under 35 U.S.C. § 119(e) to U.S. Provisional Application No. 63/074,539 filed on Sep. 4, 2020, which is hereby incorporated by reference in its entirety.

TECHNICAL FIELD

This disclosure relates generally to smart mirrors, and more particularly to method and system for analysing activity performance of users through smart mirror.

BACKGROUND

In an era of rapid urbanization and a fast-paced life, in many places, people may find it difficult to dedicate a regular time daily for physical well-being and find a right work-life balance. Moreover, in times of a pandemic, when lockdowns are imposed, gyms and parks are usually closed for public access. In such cases, it is much more convenient for a person to workout at home.

Many exercise machines and training methods are monitored and configured with adjustable parameter settings based on capabilities, goals, and specific training methods desired by a user. However, for best results and to reduce the chance of muscle damage, injuries, many exercises require correct performance of complex actions by the user during an exercise routine and skilled adjustment of weights or force resistance.

A drawback associated with a conventional workout machine is that the setting parameters used and the variations over time during the workout session can be different. Another drawback is that the exercise machine does not remember the customization settings or preferences entered earlier. Another problem is that the workout history is not preserved. Also, a conventional exercise machine may contain a set of pre-configured programs that may not be appropriate for all users. Another problem associated with a conventional exercise machine is that its pre-configured programs do not consider other parameters such as pose, movement of the body and other parts.

Further, at most gyms, there is typically a set of mirrors that allow a person to view and confirm or adjust their pose and movements to account for the proper pose and movements. However, unless the person has an expert to analyze the pose and movements, the person may perform with improper pose and movements which can result in a potential injury. Further, an exercise trainer cannot be present every time while exercising. Also, it is not possible for a trainer to monitor and guide every exerciser at the same time while performing group exercises. Further, most of the time, trainers cannot be available to motivate/encourage the exercisers.

Further, it is known that the sensors record a variety of information about the human body. For example, electromyography (EMG) electrodes can measure electrical activity generated by a person's muscles. Similarly, there are motion sensors that record the motion/movement of the person. Hence, in relation to training of individuals, and especially in relation to self-training or personal training or remote training, current technologies do not enable coaching/training entities to monitor physiological states of individuals they are coaching/training and/or efficiently manage exercise regimens for individuals in a personalized and real-time manner. Since individuals may have personalized needs in relation to improving performance, it is desirable for systems to automatically tailor metrics and instruction by taking into account physiological states.

On the other hand, since monitoring and evaluating the exercise/fitness, matching the exercise sequence, counting the sequence, tracking the real time progress of the exercise through physical presence of the instructor can be time consuming, and reliability of the results may be low according to the subjective evaluation criteria of the instructor, it is beneficial to use a mirror display, Artificial Intelligence (AI), and Augmented Reality (AR) technology to solve such a problem.

Therefore, interactive exercise machines using sensors for tracking the pose and body movement of the user and further providing an interactive smart mirror for displaying, managing the exercise are highly desirable in terms of health and fitness for many users. Besides fitness, the interactive smart mirror may also be desirable in various other scenarios, for example, rehab, physiotherapy, Yoga, dance, theatre, and other activities in which a feedback on composure and observation are important.

SUMMARY

In one embodiment, a method for analysing activity performance of a user in real-time through a smart mirror is disclosed. In one example, the method includes rendering, via a Graphical User Interface (GUI) of a smart mirror, a plurality of activity types. Each of the plurality activity types includes a plurality of activities. The method further includes receiving, via a user command, a user selection of at least one of an activity type from the plurality of activity types and an activity from the plurality of activities associated with activity type. The method further includes capturing in real-time, via at least one camera, multimedia data of current activity performance of the user corresponding to the activity type and the activity. The method further includes processing in real-time, by an Artificial Intelligence (AI) model, the captured multimedia data to determine a current field of view of the user relative to the smart mirror, based on at least one of: eye gaze of the user and orientation of the head of the user; a current pose and motion of the user based on orientation and position of the user relative to the smart mirror; a set of user performance parameters based on current activity performance of the user, wherein the AI model is configured based on target activity performance of an activity expert, and a plurality of correct and incorrect movements associated with the current activity; and an estimated future field of view of the user relative to the smart mirror based on the current field of view of the user, an estimated future eye gaze of the user, an estimated future orientation of the head of the user, and an estimated future pose and motion of the user. The method further includes generating in real-time, by the AI model, a pose skeletal model based on the current pose and estimated future field of view and the current pose and estimated future pose and motion of the user. The pose skeletal model includes a plurality of key points based on the activity type and the activity. Each of the plurality of key points corresponds to a joint of the user. The method further includes augmenting in real-time, by the AI model, a reflection of the user on the smart mirror with one of the pose skeletal model and the plurality of key points overlayed on top of the reflection, based on the current pose and estimated future field of view and the current pose and estimated future pose and motion of the user. Each of the plurality of key points is overlayed over a corresponding joint of the user in the reflection. The method further includes comparing, by the AI model, the set of user performance parameters with a set of target activity performance parameters. The set of target activity performance parameters corresponds to the activity expert. The method further includes generating, by the AI model, feedback for the user based on comparison of the set of user performance parameters with the set of target activity performance parameters. The feedback includes at least one of corrective actions or alerts. The feedback includes at least one of visual feedback, aural feedback, or haptic feedback. The method further includes rendering, by the AI model, the feedback. Rendering the feedback includes overlaying one of the at least one corrective actions over the reflection of the user on the smart mirror. Rendering the feedback further includes displaying the alerts on the GUI of the smart mirror. Rendering the feedback further includes outputting the aural feedback to the user, via a speaker configured with the smart mirror.

In one embodiment, a smart mirror for analysing activity performance of a user in real-time through a smart mirror is disclosed. In one example, the smart mirror includes a one-way mirror and a display coupled with the one-way mirror. The display includes a GUI. The GUI is configured to render a plurality of activity types. Each of the plurality activity types includes a plurality of activities. The GUI is further configured to receive, via a user command, a user selection of at least one of an activity type from the plurality of activity types and an activity from the plurality of activities associated with activity type. The smart mirror further includes at least one camera configured to capture in real-time multimedia data of current activity performance of the user corresponding to the activity type and the activity. The smart mirror further includes a processor and a memory communicatively coupled to the processor. The memory stores processor instructions, which when executed by the processor, cause the processor to process in real-time, by an AI model, the captured multimedia data to determine a current field of view of the user relative to the smart mirror, based on at least one of: eye gaze of the user and orientation of the head of the user; a current pose and motion of the user based on orientation and position of the user relative to the smart mirror; a set of user performance parameters based on current activity performance of the user, wherein the AI model is configured based on target activity performance of an activity expert, and a plurality of correct and incorrect movements associated with the current activity; and an estimated future field of view of the user relative to the smart mirror based on the current field of view of the user, an estimated future eye gaze of the user, an estimated future orientation of the head of the user, and an estimated future pose and motion of the user. The processor-executable instructions, on execution, further cause the processor to generate in real-time, by the AI model, a pose skeletal model based on the current pose and estimated future field of view and the current pose and estimated future pose and motion of the user. The pose skeletal model includes a plurality of key points based on the activity type and the activity. Each of the plurality of key points corresponds to a joint of the user. The processor-executable instructions, on execution, further cause the processor to augment in real-time, by the AI model, a reflection of the user on the smart mirror with one of the pose skeletal model and the plurality of key points overlayed on top of the reflection, based on the current pose and estimated future field of view and the current pose and estimated future pose and motion of the user. Each of the plurality of key points is overlayed over a corresponding joint of the user in the reflection. The processor-executable instructions, on execution, further cause the processor to compare, by the AI model, the set of user performance parameters with a set of target activity performance parameters. The set of target activity performance parameters corresponds to the activity expert. The processor-executable instructions, on execution, further cause the processor to generate, by the AI model, feedback for the user based on comparison of the set of user performance parameters with the set of target activity performance parameters. The feedback includes at least one of corrective actions or alerts. The feedback includes at least one of visual feedback, aural feedback, or haptic feedback. The processor-executable instructions, on execution, further cause the processor to render, by the AI model, the feedback. To render the feedback, the processor-executable instructions, on execution, further cause the processor to overlay one of the at least one corrective actions over the reflection of the user on the smart mirror. To render the feedback, the processor-executable instructions, on execution, further cause the processor to display the alerts on the GUI of the smart mirror. To render the feedback, the processor-executable instructions, on execution, further cause the processor to output the aural feedback to the user, via a speaker configured with the smart mirror.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIGS. 1A-11 illustrate a block diagram of an exemplary smart mirror for analysing activity performance of a user in real-time through a smart mirror, in accordance with some embodiments.

FIG. 2 illustrates a functional block diagram of an exemplary system for analysing activity performance of a user in real-time through a smart mirror, in accordance with some embodiments.

FIG. 4 illustrates a flow diagram of an exemplary process for correcting initial position of a user, in accordance with some embodiments.

FIG. 5 illustrates a flow diagram of an exemplary process for comparing trainer avatar corresponding to target activity performance with and user avatar corresponding to current activity performance of a user, in accordance with some embodiments.

FIG. 6 illustrates an exemplary Graphical User Interface (GUI) displaying a plurality of exercises, in accordance with some embodiments.

FIG. 7 illustrates an exemplary GUI displaying a home page of a fitness application, in accordance with some embodiments.

FIG. 8 illustrates an exemplary Graphical User Interface (GUI) displaying exercise parameters, in accordance with some embodiments.

FIG. 9 illustrates an exemplary GUI displaying current activity performance and pose skeletal model of the user, in accordance with some embodiments.

FIG. 10 illustrates an exemplary GUI displaying current activity performance and pose skeletal model of the user, in accordance with some embodiments.

FIG. 11 illustrates an exemplary GUI displaying current activity performance and pose skeletal model of the user, in accordance with some embodiments.

DETAILED DESCRIPTION

Figure 1A:
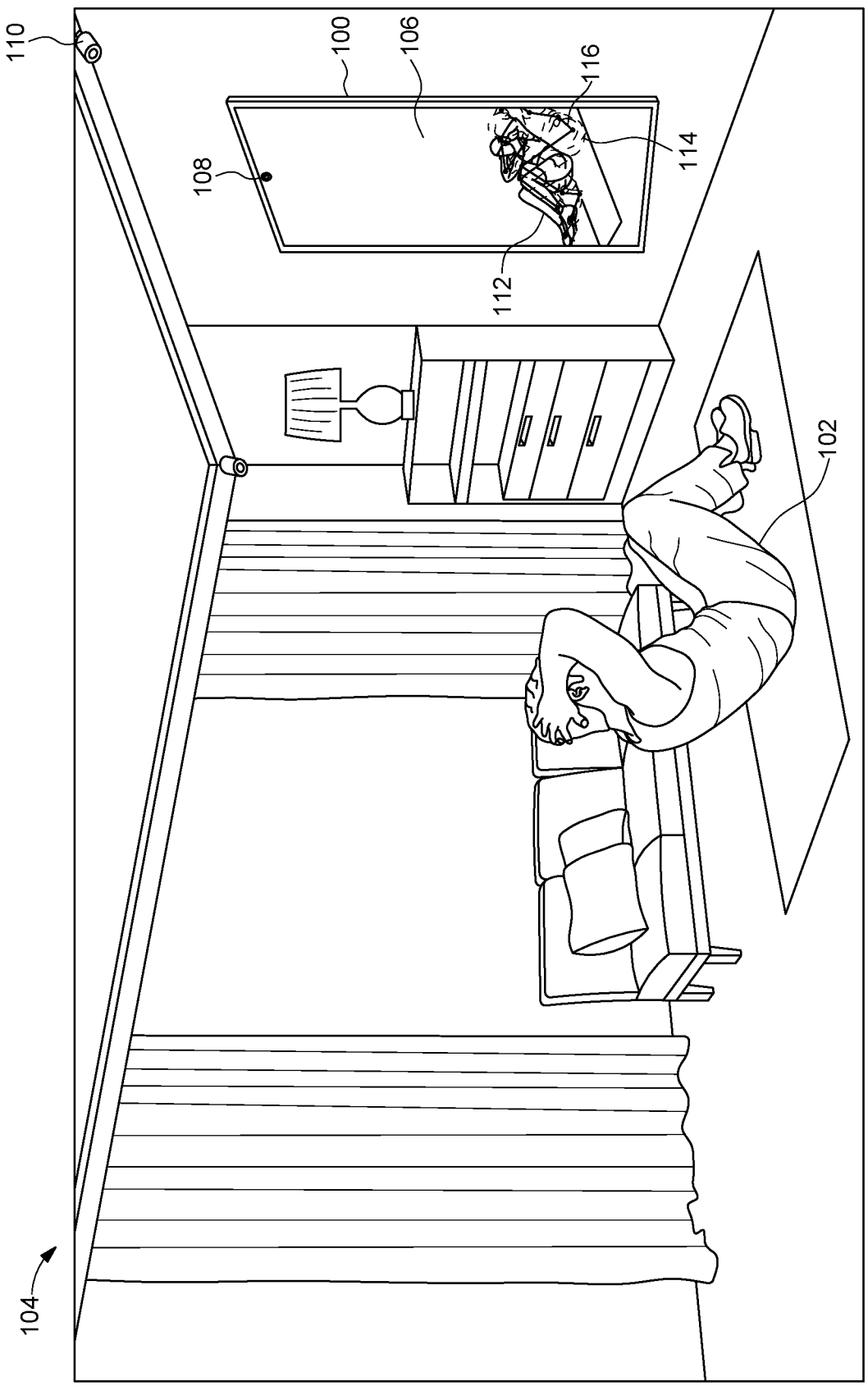

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to FIGS. 1A-11, an exemplary smart mirror 100 for analysing activity performance of a user 102 in real-time is illustrated, in accordance with some embodiments. In an exemplary scenario, user 102 may use the smart mirror 100 inside a room 104. The room 104 may be a part of, for example, a gymnasium, a physiotherapy facility, a rehab facility, a Yoga studio, physical rehabilitation centers, dojos, martial arts centers a dance studio, a theatre coaching centre, or the like. The gymnasium may include a plurality of smart mirrors configured for analysing activity performance of a plurality of users. In yet another embodiment, the smart mirror 100 may be used in an outdoor environment (for example, a public park). In some embodiments, the smart mirror 100 may be used to monitor progress of patients undergoing rehab or physiotherapy.

The smart mirror 100 may include a one-way mirror 106, a display coupled with the one-way mirror 106, at least one camera 108, at least one external camera 110, one or more processors (not shown in figure), and a memory (not shown in figure) communicatively coupled with the one or more processors. In an embodiment, the display is positioned behind the one-way mirror 106. It may be noted that the display may be of equal or nearly equal dimensions as the one-way mirror 106. The display may include a Graphical User Interface (GUI). It may be noted that the at least one camera 108 may be positioned at center, along an edge, or at bottom of the smart mirror 100. The smart mirror 100 may analyse activity performance of a user in real-time using multimedia data captured by the at least one camera 108 and the at least one external camera 110.

As will be described in greater detail in conjunction with FIGS. 2-11, the smart mirror 100 renders, via a GUI of a smart mirror 100, a plurality of activity types. Each of the plurality activity types includes a plurality of activities. The smart mirror 100 further receives, via a user command, a user selection of at least one of an activity type from the plurality of activity types and an activity from the plurality of activities associated with activity type. The smart mirror 100 further captures in real-time, via at least one camera, multimedia data of current activity performance of the user 102 corresponding to the activity type and the activity. The smart mirror 100 further processes in real-time, by an Artificial Intelligence (AI) model, the captured multimedia data to determine a current field of view of the user 102 relative to the smart mirror, based on at least one of: eye gaze of the user 102 and orientation of the head of the user 102; a current pose and motion of the user 102 based on orientation and position of the user 102 relative to the smart mirror 100; a set of user performance parameters based on current activity performance of the user 102, wherein the AI model is configured based on target activity performance of an activity expert, and a plurality of correct and incorrect movements associated with the current activity; and an estimated future field of view of the user 102 relative to the smart mirror based on the current field of view of the user 102, an estimated future eye gaze of the user 102, an estimated future orientation of the head of the user 102, and an estimated future pose and motion of the user 102. The smart mirror 100 further generates in real-time, by the AI model, a pose skeletal model based on the current pose and estimated future field of view and the current pose and estimated future pose and motion of the user 102. The pose skeletal model includes a plurality of key points based on the activity type and the activity. Each of the plurality of key points corresponds to a joint of the user 102. The smart mirror 100 further augments in real-time, by the AI model, a reflection of the user 102 on the smart mirror with one of the pose skeletal model and the plurality of key points overlayed on top of the reflection, based on the current pose and estimated future field of view and the current pose and estimated future pose and motion of the user 102. Each of the plurality of key points is overlayed over a corresponding joint of the user 102 in the reflection. The smart mirror 100 further compares, by the AI model, the set of user performance parameters with a set of target activity performance parameters. The set of target activity performance parameters corresponds to the activity expert. The smart mirror 100 further generates, by the AI model, feedback for the user 102 based on comparison of the set of user performance parameters with the set of target activity performance parameters. The feedback includes at least one of corrective actions or alerts. The feedback includes at least one of visual feedback, aural feedback, or haptic feedback. The smart mirror 100 further renders, by the AI model, the feedback. Rendering the feedback includes overlaying one of the at least one corrective actions over the reflection of the user 102 on the smart mirror 100. Rendering the feedback further includes displaying the alerts on the GUI of the smart mirror 100. Rendering the feedback further includes outputting the aural feedback to the user 102, via a speaker configured with the smart mirror 100.

The memory may include the AI model. Further, the memory may store instructions that, when executed by the one or more processors, cause the one or more processors to analyse activity performance of the user 102 in real-time through the smart mirror 100, in accordance with aspects of the present disclosure. The memory may also store various data (for example, AI model data, a plurality of activity types, a plurality of activities, multimedia data, set of user performance parameters, target activity performance data, and the like) that may be captured, processed, and/or required by the smart mirror 100.

The smart mirror 100 may interact with the user 102 via the GUI accessible via the display. By way of an example, the display may be a Liquid crystal display (LCD), a Light-emitting diode (LED) backlit LCD, a Thin-Film Transistor (TFT) LCD, an LED display, an Organic LED (OLED) display, an Active Matrix Organic LED (AMOLED) display, a Plasma Display Panel (PDP) display, a Quantum Dot LED (QLED) display, or the like. The smart mirror 100 may also include one or more external devices (not shown in figure). In some embodiments, the smart mirror 100 may interact with the one or more external devices over a communication network (for example, a Universal Serial Bus (USB) data cable, a High Definition Multimedia Interface (HDMI) cable, Wireless Fidelity (Wi-Fi), Light Fidelity (Li-Fi), Bluetooth, and other similar communication networks) for sending or receiving various data. The external devices may include, but may not be limited to, a remote server, a digital device, or another computing system.

The GUI renders a plurality of activity types for the user 102. Each of the plurality of activity types includes a plurality of activities. The user 102 may select at least one of an activity type from the plurality of activity types and an activity from the plurality of activities associated with activity type via a user command. Further, the smart mirror 100 initiates the activity. The GUI displays a target activity performance 112 corresponding to an activity expert on the screen. The target activity performance 112 may be a video recording of the activity expert, a 3-Dimensional (3D) model of the activity expert, a 2-Dimensional (2D) model, or a 4-Dimensional (4D) of the activity expert. The user 102 may follow the target activity performance 112 with a current activity performance. The one-way mirror 106 shows a reflection 114 of the current activity performance of the user 102.

Further, the at least one camera 108 and the at least one external camera 110 capture multimedia data associated with the current activity performance of the user 102. The at least one external camera 110 enhances accuracy of determination of pose, movement, gaze, and orientation of head of the user 102. Additionally, the at least one camera 108 may be used for facial recognition of the user 102. Facial data corresponding to the user 102 is associated with a user profile. The user profile is stored in the database and may be associated with current and historical user data such as, but not limited to, history, custom settings, messages from the activity expert, profile data, and other similar user data.

Further, the AI model receives the multimedia data and processes the multimedia data to determine a current field of view of the user 102 relative to the smart mirror 100, a current pose and motion of the user 102, a set of user performance parameters, and an estimated future field of view of the user 102 relative to the smart mirror 100. The AI mode, for example, may be an AI predictive model. The current field of view of the user 102 relative to the smart mirror 100 is determined based on at least one of eye gaze of the user 102 and orientation of the head of the user 102. The current pose and motion of the user 102 is determined based on orientation and position of the user 102 relative to the smart mirror 100. The set of user performance parameters is determined based on the current activity performance of the user 102. The AI model is configured based on target activity performance 112 of the activity expert, and a plurality of correct and incorrect movements associated with the current activity. The estimated future field of view of the user 102 relative to the smart mirror 100 is determined based on the current field of view of the user 102, an estimated future eye gaze of the user 102, an estimated future orientation of the head of the user 102, and an estimated future pose and motion of the user 102. In an embodiment, the smart mirror 100 is configured to automatically adjust at an angle based on the estimated future orientation of the head of the user 102. For example, when the user 102 is performing the current activity in a lying down position, the smart mirror 100 may rotate by about 90 degrees to provide an improvised tracking of the current activity performance.

Further, the AI model generates a pose skeletal model 116 based on the current pose and estimated future field of view and the current pose and estimated future pose and motion of the user 102. The pose skeletal model 116 includes a plurality of key points based on the activity type and the activity. Each of the plurality of key points corresponds to a joint or a feature of the user 102. Additionally, the plurality of key points may be connected with lines representing bones of the user 102 to complete the pose skeletal model 116.

Further, the AI model augments in real-time, the reflection 114 of the user 102 on the one-way mirror 106 with one of the pose skeletal model 116 and the plurality of key points overlaid on top of the reflection 114, based on the current pose and estimated future field of view and the current pose and estimated future pose and motion of the user 102. Each of the plurality of key points is overlaid over a corresponding joint or a feature of the user 102 in the reflection 114. Therefore, the one-way mirror 106 shows the reflection 114 of the current activity performance of the user 102. The display of the smart mirror 100 shows the pose skeletal model 116 overlaid on top of the reflection 114 of the user, and the target activity performance 112 of the activity expert overlayed on the reflection 114 of the user. Additionally, the display of the smart mirror 100 may show a set of user performance parameters associated with the current activity performance, and a set of target activity parameters associated with the target activity performance 112. However, for the sake of brevity, the set of user performance parameters and the set of target activity parameters are not shown in the illustrated figures. It may be noted that the pose skeletal model 116 is automatically adjusted and normalized with respect to the reflection 114 of the user 102 based on an estimated future distance of the user 102 relative to the smart mirror 100, the current pose and estimated future field of view, and the current pose and estimated future pose and motion of the user 102. In some embodiments, transparency of the pose skeletal model 116 may be adjustable by the user 102. In an embodiment, the pose skeletal model 116 is completely transparent and invisible to the user 102. In such an embodiment, the pose skeletal model 116 may be used by the AI model solely for computational purposes.

The AI model compares the set of user performance parameters with a set of target activity performance parameters. Further, the AI model generates a feedback for the user 102 based on comparison of the set of user performance parameters with the set of target activity performance parameters. The feedback includes at least one of corrective actions or alerts. The feedback may be at least one of visual feedback, graphic feedback, aural feedback, or haptic feedback. Further, the AI model renders the feedback. The rendering may include overlaying one of the at least one corrective actions over the reflection of the user 102 on the smart mirror 100. Further, the rendering may include displaying the alerts on the GUI of the smart mirror 100. Further, the rendering may include outputting the aural feedback to the user 102, via a speaker configured with the smart mirror 100. The feedback may include generating a warning to the user 102 including indication for correcting the current pose of the user 102, indication for correcting user motion associated with the current pose of the user 102, and indication for correcting the current position of the user 102, when the user 102 is at least partially outside a field of view of the at least one camera 108.

In FIG. 1A, the user 102 follows the target activity performance 112 correctly as shown on the display. The current activity performance of the user 102, and the associated pose skeletal model 116, is in accordance with the target activity performance 112 of the activity expert. Therefore, the smart mirror 100 may continue to display the target activity performance 112 as long as the current activity performance is in accordance with the target activity performance 112. In some embodiments, the smart mirror 100 may output a motivational audio message encouraging the user 102 to keep the current activity performance in accordance with the target activity performance 112.

Figure 1B:
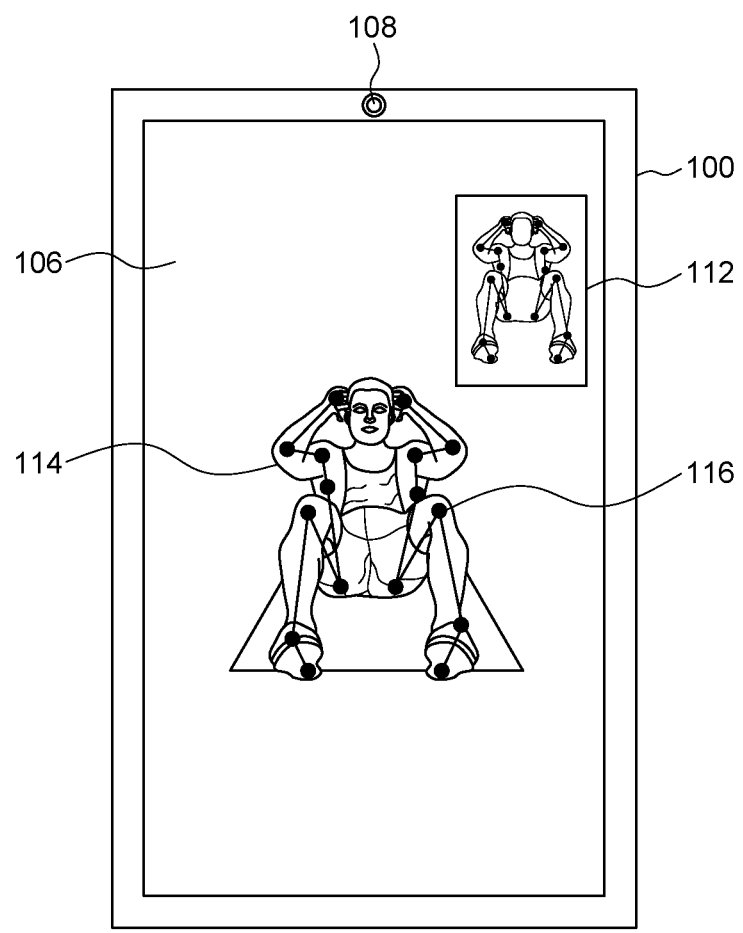

In FIG. 1B, a front view of the smart mirror 100 is shown when the user 102 follows the target activity performance 112 correctly as shown on the display. The target activity performance 112 is shown in an inset frame on the display of the smart mirror 100. Further, the reflection 114 of the user 102 may be shown by the one-way mirror 106. The multimedia data corresponding to the current activity performance of the user 102 may be captured in real-time by the at least one camera 108. Further, the AI model of the smart mirror 100 may process the multimedia data and generate the pose skeletal model 116. Since the current activity performance of the user 102 is in accordance with the target activity performance 112, the smart mirror 100 may continue to display the target activity performance 112 in the inset frame as long as the current activity performance is in accordance with the target activity performance 112. In some embodiments, the smart mirror 100 may output a motivational audio message encouraging the user 102 to keep the current activity performance in accordance with the target activity performance 112.

Figure 1C:
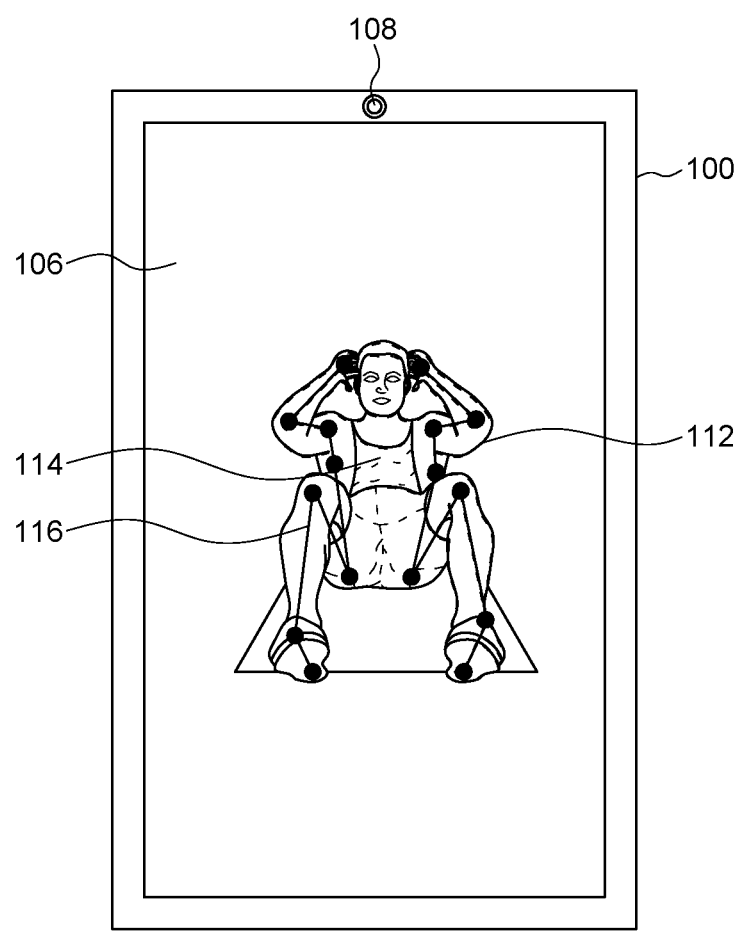

In FIG. 1C, a front view of the smart mirror 100 is shown when the user 102 follows the target activity performance 112 correctly as shown on the display. The target activity performance 112 is shown on the display of the smart mirror 100. Further, the reflection 114 of the user 102 may be shown by the one-way mirror 106. The target activity performance 112 is overlayed upon the reflection 114 of the user 102 shown by the one-way mirror 106. The multimedia data corresponding to the current activity performance of the user 102 may be captured in real-time by the at least one camera 108. Further, the AI model of the smart mirror 100 may process the multimedia data and generate the pose skeletal model 116. In some embodiments, the AI model may determine distance of the user 102 from the smart mirror 100, a current pose and estimated future gaze of the user 102 and a current pose and estimated future pose and movement of the user 102. The AI model may adjust and normalize the display of the target activity performance 112 and the pose skeletal model 116 in accordance with the current pose and estimated future gaze of the user 102 to avoid any parallax issues and error. Since the current activity performance of the user 102 is in accordance with the target activity performance 112, the smart mirror 100 may continue to display the target activity performance 112 as long as the current activity performance is in accordance with the target activity performance 112. In some embodiments, the smart mirror 100 may output a motivational audio message encouraging the user 102 to keep the current activity performance in accordance with the target activity performance 112.

Figure 1D:
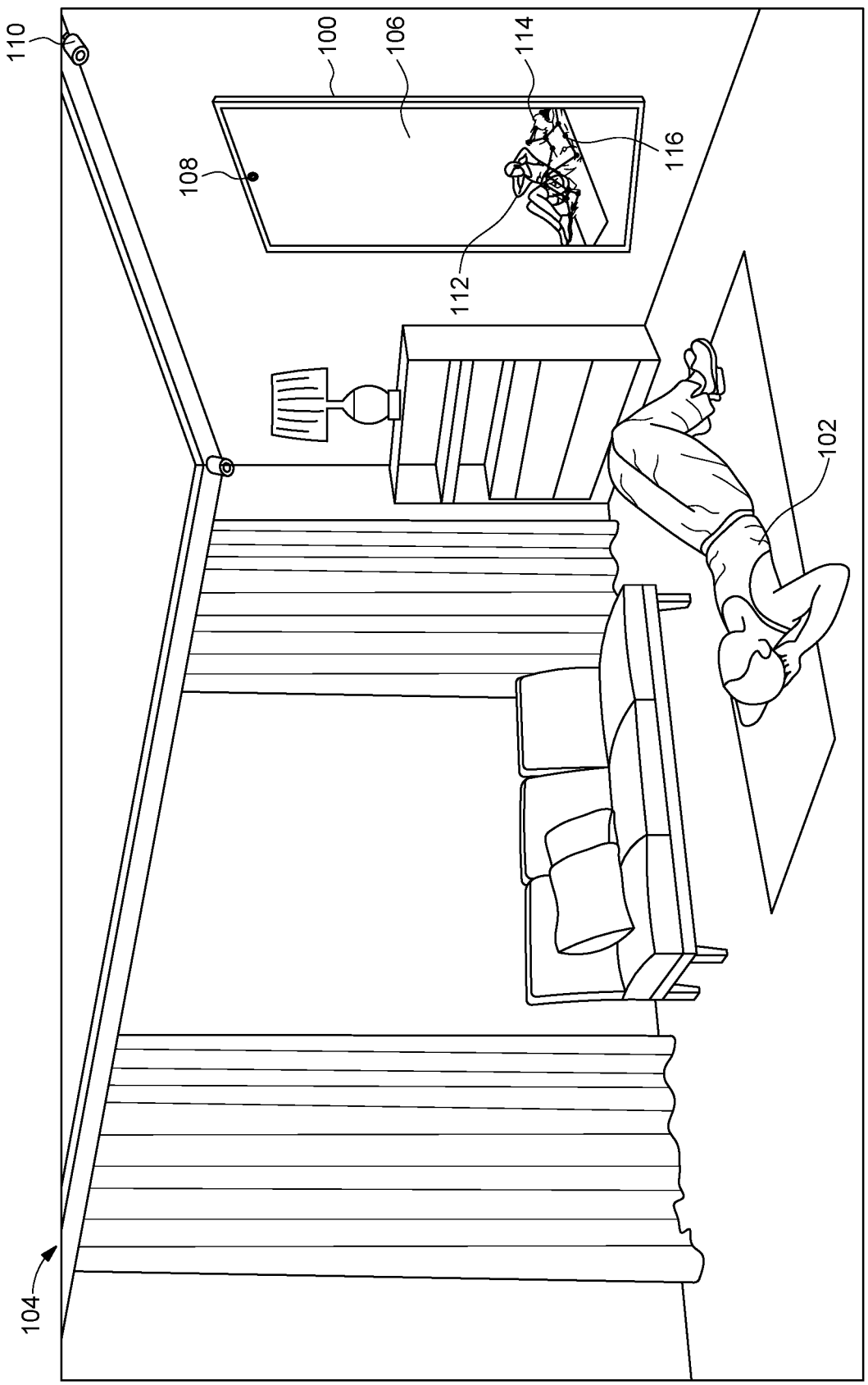

In FIG. 1D, the user 102 fails to follow the target activity performance 112 correctly as shown on the display. The current activity performance of the user 102, and the associated pose skeletal model 116, shows a deviation from the target activity performance 112 of the activity expert. The target activity performance 112 of the activity expert is in a sitting position, while the user in a lying down position. Therefore, the smart mirror 100 may generate feedback for the user 102 to ensure that the current activity performance is in accordance with the target activity performance 112. When the deviation of the current activity performance is above a predefined threshold performance and continues for a predefined threshold time, the smart mirror 100 may pause the display of the set of user performance parameters and the target activity performance 112.

Figure 1E:
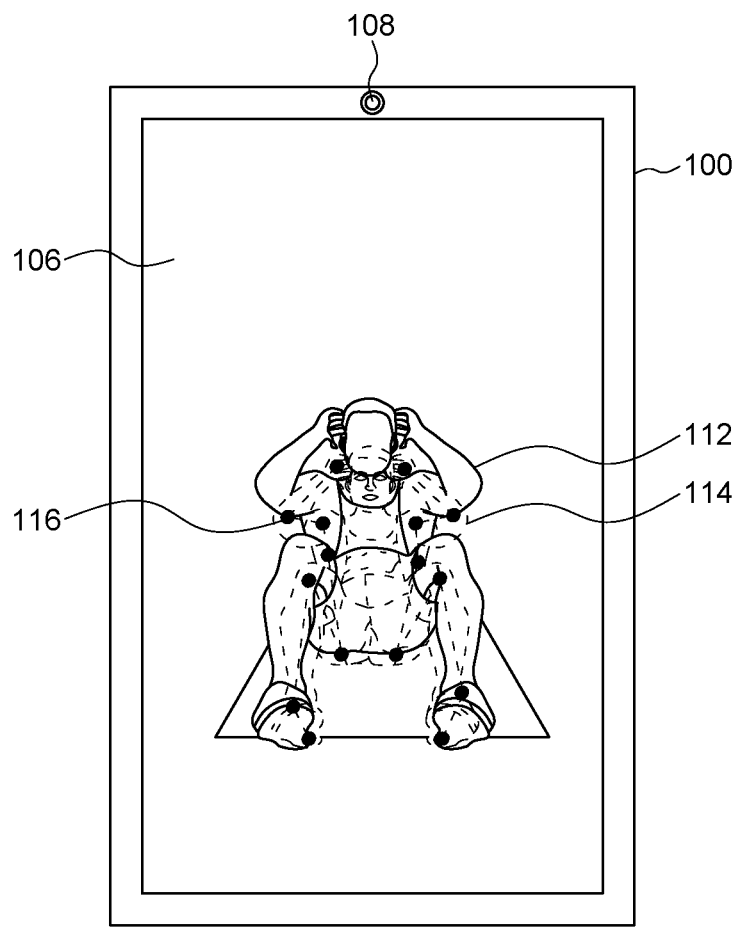

In FIG. 1E, a front view of the smart mirror 100 is shown when the user 102 fails to follow the target activity performance 112 correctly as shown on the display. The target activity performance 112 of the activity expert is in a sitting position, while the user in a lying down position. When the current activity performance of the user 102 deviates from the target activity performance 112 above a predefined performance threshold, the smart mirror 100 may generate a feedback (video, graphical, aural, or haptic) for the user 102 to ensure that the current activity performance is in accordance with the target activity performance 112. When the deviation of the current activity performance is above a predefined threshold performance and continues for a predefined threshold time, the smart mirror 100 may pause the display of the set of user performance parameters and the target activity performance 112.

Figure 1F:
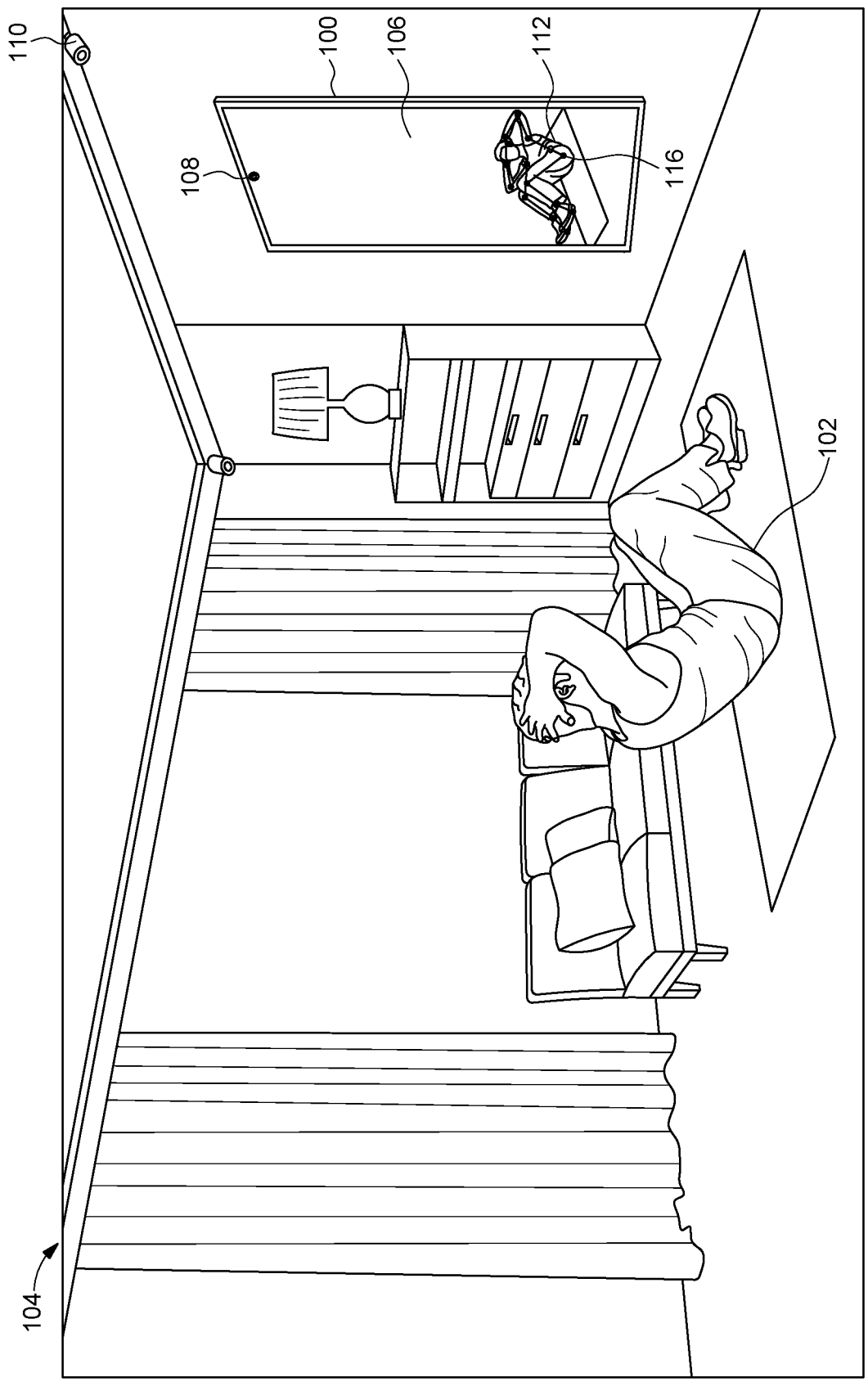

In FIG. 1F, the smart mirror 100 displays the multimedia data associated with the user 102. In such an embodiment, the multimedia data of the user 102 shown by the display is more prominently visible to the user 102 than the reflection of the user 102 by the one-way mirror 106. Pose and informational data may be shown as a video stream, a 2D model, a 3D model, or a model of the user 102 in space (2D or 3D), time, and based on performance indicators. The user 102 follows the target activity performance 112 correctly as shown on the display overlayed upon the multimedia data of the user 102. The current activity performance of the user 102, and the associated pose skeletal model 116, is in accordance with the target activity performance 112 of the activity expert. Therefore, the smart mirror 100 may continue to display the target activity performance 112 as long as the current activity performance is in accordance with the target activity performance 112. In an embodiment, the multimedia data of the user 102 is not shown on the display. In such an embodiment, the pose skeletal model 116 of the user 102 is overlayed on the target activity performance 112. In another embodiment, a pose skeletal model corresponding to the target activity performance 112 is shown on the display overlayed upon the multimedia data of the current activity performance of the user 102 and the associated pose skeletal model 116.

Figure 1G:
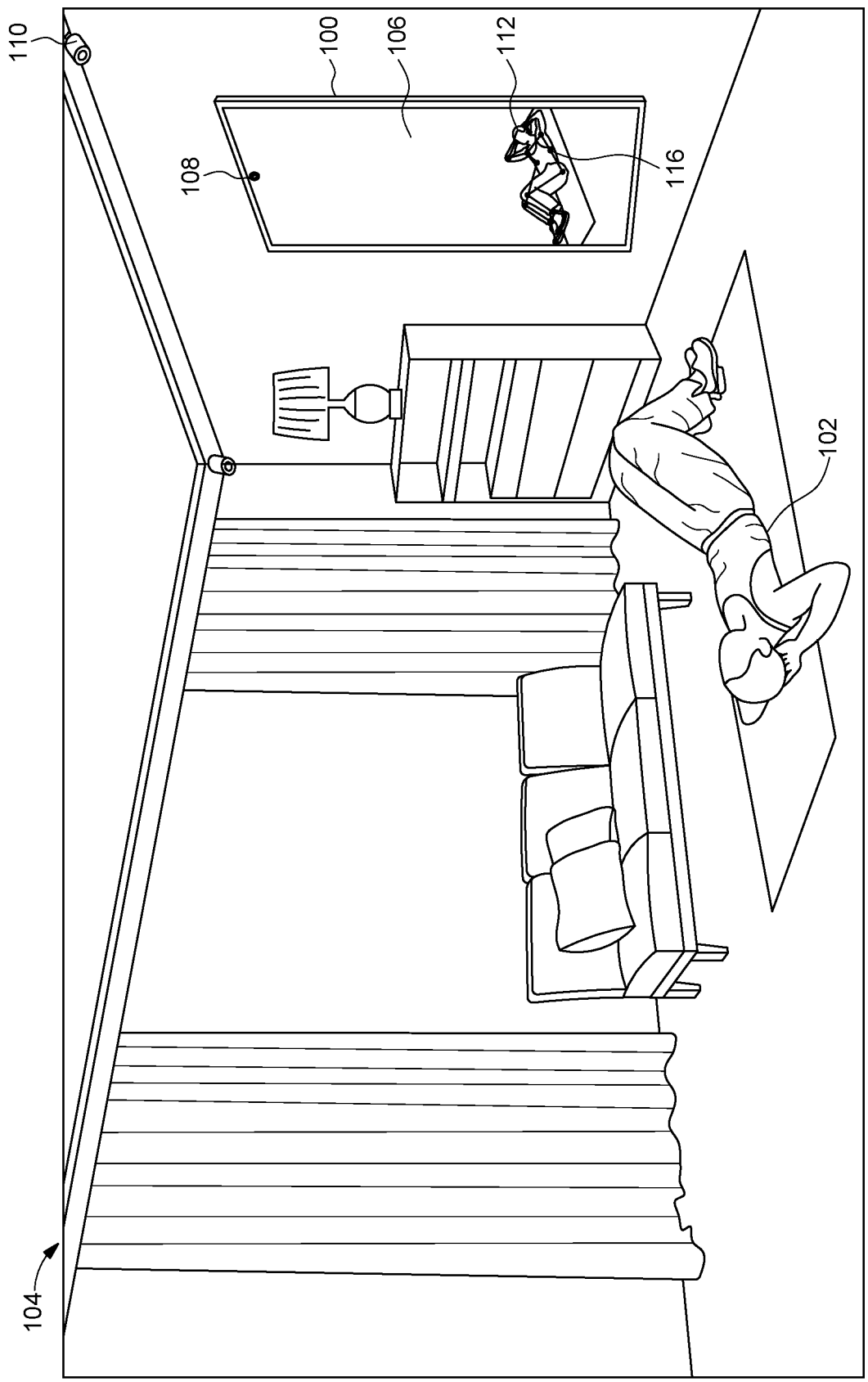

In FIG. 1G, the smart mirror 100 displays the multimedia data associated with the user 102. In such an embodiment, the multimedia data of the user 102 shown by the display is more prominently visible to the user than the reflection of the user by the one-way mirror 106. the user fails to follow the target activity performance 112 correctly as shown on the display. The current activity performance of the user, and the associated pose skeletal model 116, shows a deviation from the target activity performance 112 of the activity expert. Therefore, the smart mirror may generate feedback for the user to ensure that the current activity performance is in accordance with the target activity performance 112. When the deviation of the current activity performance is above a predefined threshold performance and continues for a predefined threshold time, the smart mirror may pause the display of the set of user performance parameters and the target activity performance 112. In an embodiment, the multimedia data of the user 102 is not shown on the display. In such an embodiment, the pose skeletal model 116 of the user 102 is overlayed on the target activity performance 112. In another embodiment, a pose skeletal model corresponding to the target activity performance 112 is shown on the display overlayed upon the multimedia data of the current activity performance of the user 102 and the associated pose skeletal model 116.

Figure 1H:
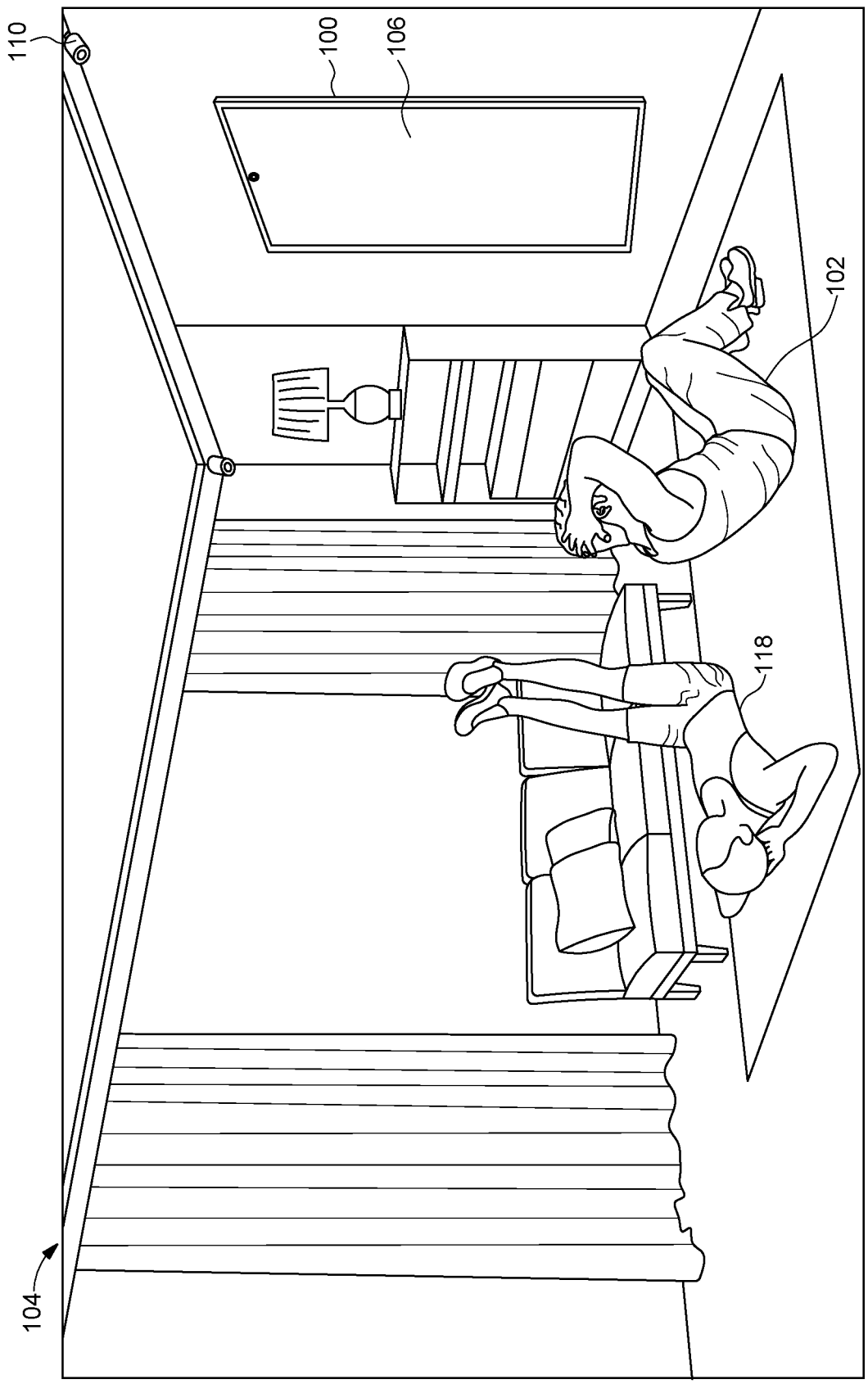

In FIG. 1H, the smart mirror 100 analyses activity performance of each of the user 102 and a user 118 simultaneously in real-time. It may be noted that the smart mirror 100 may analyze activity performance of each of a plurality of users simultaneously. For example, the smart mirror 100 may be shared by family members at home, gym members, patients underdoing rehab therapy and/or physiotherapy at a hospital, and the like. The current activity performance of the user 102 is different from the current activity performance of the user 118. The smart mirror 100 displays the target activity performance corresponding to the activity selected by each of the user 102 and the user 118. Further, the smart mirror 100 may display a pose skeletal model overlayed upon a reflection of each of the user 102 and the user 118. In some embodiments, the smart mirror 100 displays the target activity performance overlayed upon the reflection of each of the user 102 and the user 118. In some embodiment, the smart mirror 100 displays the target activity performance in an inset frame on the display. Alternately, the smart mirror 100 may include a plurality of displays or screens for each of a plurality of users (for example, the user 102 and the user 118). A single display or screen in such a smart mirror 100 may be used by one user at a time.

Figure 1I:
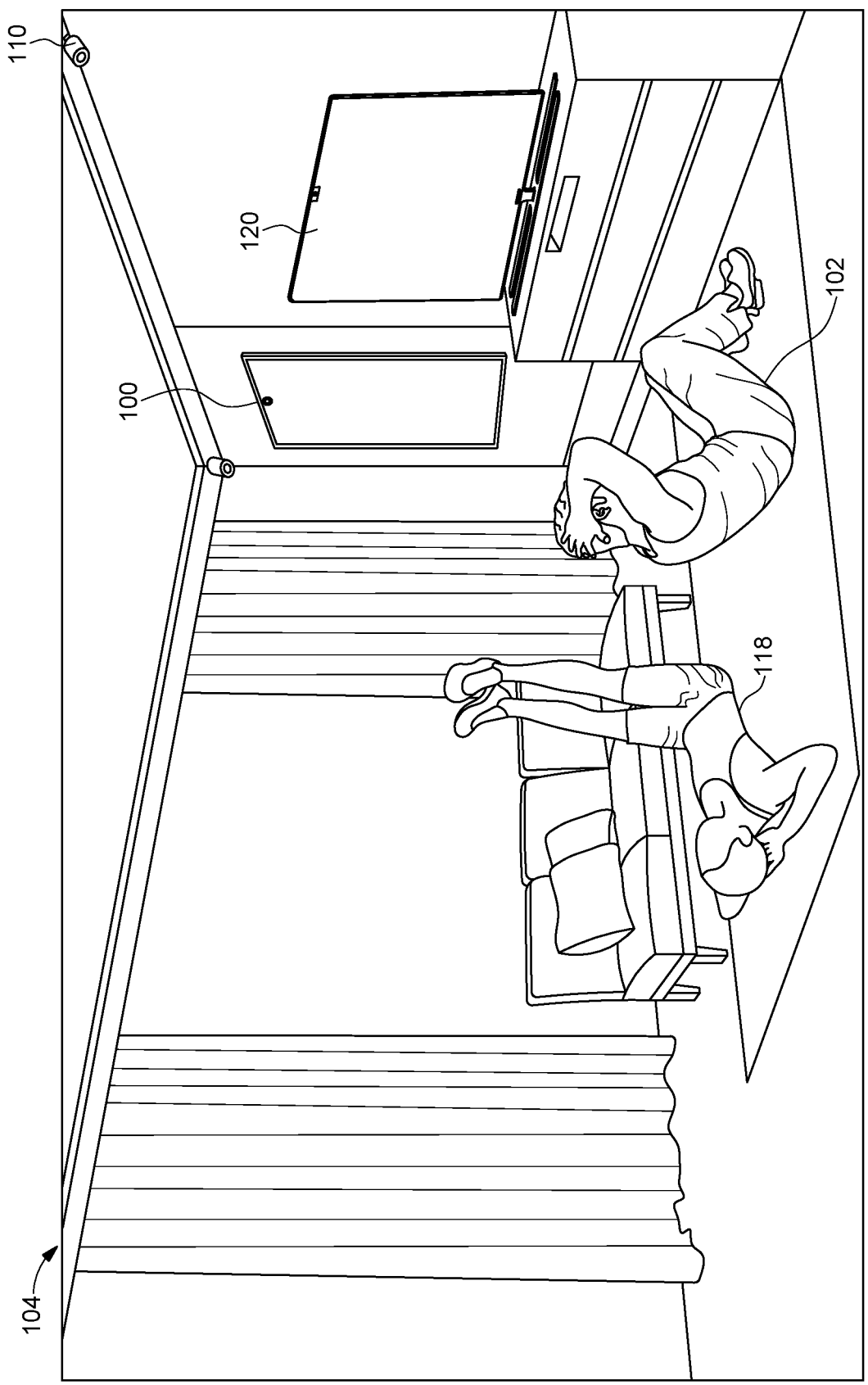

In FIG. 1I, the smart mirror 100 analyses the activity performance of the user 102 and a display device 120 (for example, a smart Television (TV), a projector screen, a desktop monitor, and other similar display devices) analyses the activity performance of the user 118. The display device 120 includes a camera and a GUI. Functioning of the display device 120 is similar to the smart mirror 100. The smart mirror 100 shows the reflection or the multimedia data corresponding to the user 102 and the display device 120 displays multimedia data corresponding to the user 118. The display device 120 may be communicatively coupled with the smart mirror 100. In an embodiment, a combination of a plurality of devices (such as, the smart mirror and the display device 120) may be used in a public setting (for example, a gymnasium or a public park) for a plurality of users.

Figure 2:
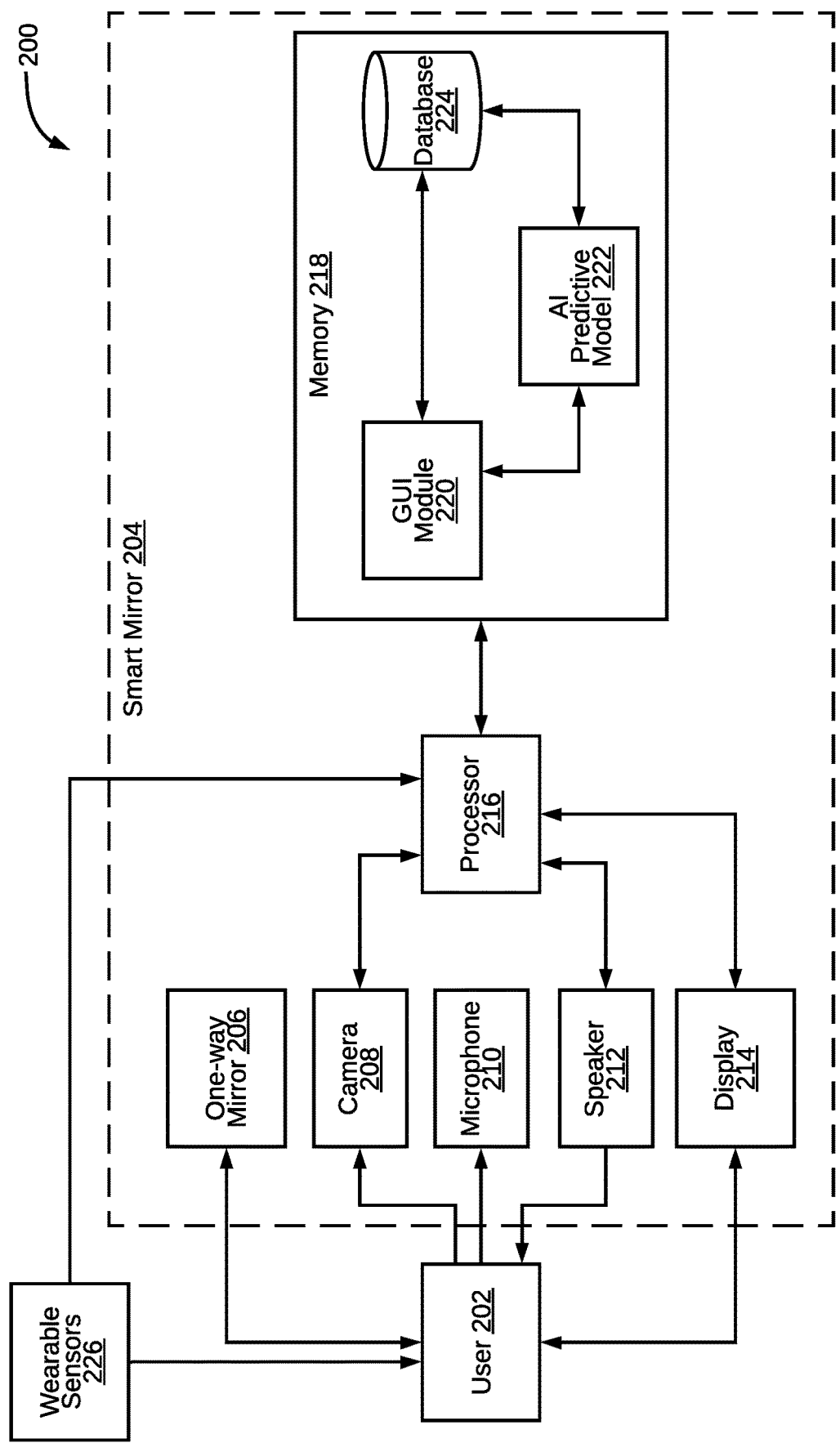

Referring now to FIG. 2, a functional block diagram of an exemplary system 200 for analyzing activity performance of a user 202 in real-time through a smart mirror 204 is illustrated, in accordance with some embodiments. In some embodiments, the smart mirror 204 of the system 200 is analogous to the smart mirror 100. The smart mirror 204 includes a one-way mirror 206, a camera 208, a microphone 210, a speaker 212, a display 214, a processor 216, and a memory 218. The memory 218 includes a GUI module 220, an AI model 222, and a database 224. One or more wearable sensors 226 may be worn by the user 202. By way of example, the one or more wearable sensors 226 include an Electrocardiogram (ECG) sensor, an Electroencephalogram (EEG) sensor, an Electromyography (EMG) sensor, a pulse oximeter, and the like. Each of the one or more wearable sensors 226 is communicatively coupled with the smart mirror 204 via a communication network. Further, the smart mirror 204 may include one or more in-built sensors (for example, proximity sensor, audio sensor, Light Detection and Ranging (LIDAR) sensor, Infrared (IR) sensor, and other similar motion based sensors) to receive additional data that may be processed and analyzed for the user 202.

The display 214 is coupled with the one-way mirror 206. The one-way mirror 206 covers the display 214. Further, the one-way mirror 206 is configured to partially reflect an image of the user 202 and partially show the display 214 to the user 202. Therefore, the one-way mirror 206 acts as a semi-reflective surface for the user 202 and acts as a semi-transparent surface for the display 214. The display 214 may be of same dimensions as the one-way mirror 206. In an embodiment, length of the one-way mirror 206 may be higher than width of the one-way mirror 206. The smart mirror 204 may include a plurality of displays and a plurality of cameras to handle multiple users simultaneously.

The GUI module 220 is accessible to the user 202 via the display 214. The GUI module 220 provides a plurality of activity types to the user 202. By way of an example, the plurality of activity types may include, but may not be limited to, physical exercises, guided meditations, Yoga, physiotherapy, flower arranging, origami, dance, theatre, any form of performing arts, martial arts, speech therapy, rehab, physical therapy and rehabilitation, CROSSFIT®, LES MILLS®, F45®, ZUMBA®, BIKRAM YOGA®, ORANGE THEORY®, drawing, painting, or the like. Each of the plurality activity types includes a plurality of activities. The user 202 may select, via a user command, at least one of an activity type from the plurality of activity types and an activity from the plurality of activities associated with activity type. The user command may be at least one of a voice command (received via the microphone 210), a touch gesture, an air gesture, eye gesture, or a signal generated by an input device (for example, a mouse, a touch pad, a stylus, a keyboard, associated connected device or controller (such as, a gaming controller), or the like).

Further, the camera 208 captures in real-time, multimedia data of current activity performance of the user 202 corresponding to the activity type and the activity. In some embodiments, the smart mirror 204 may include one or more additional cameras. The multimedia data received from the camera 208 is stored in the database 224. In some embodiments, the user may edit the multimedia data based on one or more user commands. The user command may be at least one of a text command, voice command, touch command, or a visual gesture. The one or more user commands include at least one of setting a start point of the multimedia data, setting an end point of the multimedia data, removing background from the multimedia data, assigning one or more tags to the multimedia data, and sharing the multimedia data with a set of other users.

Further, the AI model 222 receives the multimedia data from the camera 208 through the processor 216 and processes the multimedia data to determine a current field of view of the user 202 relative to the smart mirror, a current pose and motion of the user 202, a set of user performance parameters, and an estimated future field of view of the user 202 relative to the smart mirror 204. The current field of view of the user 202 relative to the smart mirror is determined based on at least one of eye gaze of the user 202 and orientation of the head of the user 202. The current pose and motion of the user 202 is determined based on orientation and position of the user 202 relative to the smart mirror 204. The set of user performance parameters is determined based on the current activity performance of the user 202. The AI model 222 is configured based on target activity performance of the activity expert, and a plurality of correct and incorrect movements associated with the current activity. The estimated future field of view of the user 202 relative to the smart mirror is determined based on the current field of view of the user 202, an estimated future eye gaze of the user 202, an estimated future orientation of the head of the user 202, and an estimated future pose and motion of the user 202.

Further, the AI model 222 generates a pose skeletal model (such as, the pose skeletal model 116) based on the current pose and estimated future field of view and the current pose and estimated future pose and motion of the user 202. The pose skeletal model includes a plurality of key points based on the activity type and the activity. Each of the plurality of key points corresponds to a joint or a feature of the user 202. Additionally, the plurality of key points may be connected with lines representing bones of the user 202 to complete the pose skeletal model. In an embodiment, a 3D rendering of the user 202 may be generated as the pose skeletal model.

Further, the AI model 222 augments in real-time, the reflection of the user 202 on the one-way mirror 206 with one of the pose skeletal model and the plurality of key points overlayed on top of the reflection, based on the current pose and estimated future field of view and the current pose and estimated future pose and motion of the user 202. Each of the plurality of key points is overlayed over a corresponding joint of the user 202 in the reflection. Therefore, the one-way mirror 206 shows the reflection of the current activity performance of the user 202. The display of the smart mirror 204 shows the pose skeletal model overlayed on top of the reflection of the user 202, the target activity performance of the activity expert overlayed on the reflection of the user 202, a set of user performance parameters associated with the current activity performance, and a set of target activity parameters associated with the target activity performance. It may be noted that the pose skeletal model is automatically adjusted and normalized with respect to the reflection of the user 202 based on a current pose and estimated future distance and viewing position of the user 202 relative to the smart mirror 204, the current pose and estimated future field of view, and the current pose and estimated future pose and motion of the user 202. In some embodiments, transparency of the pose skeletal model may be adjustable by the user 202. In an embodiment, the pose skeletal model is completely transparent and invisible to the user 202. In such an embodiment, the pose skeletal model may be used by the AI model 222 solely for computational purposes.

The AI model 222 compares the set of user performance parameters with a set of target activity performance parameters. Further, feedback for the user is generated via pose and AI deviation process, based on comparison of the set of user performance parameters with the set of target activity performance parameters. The feedback includes at least one of corrective actions or alerts. The feedback may be at least one of visual feedback, aural feedback, or haptic feedback. Further, the AI model 222 renders the feedback. The rendering may include overlaying one of the at least one corrective actions over the reflection of the user 202 on the smart mirror. Further, the rendering may include displaying the alerts on the GUI of the smart mirror. Further, the rendering may include outputting the aural feedback to the user 202, via the speaker 212. In an embodiment, the speaker 212 may be a directional speaker to provide a more personalized training experience for the user 202. In some embodiments, the system 200 includes a plurality of speakers (for example, a home theatre system) installed in different regions of the room. In some embodiments, the smart mirror 204 is configured to output audio feedback via a Bluetooth headset or speaker. The feedback may include generating a warning to the user 202 including indication for correcting the current pose of the user 202, indication for correcting user motion associated with the current pose of the user 202, and indication for correcting the current position of the user 202, when the user 202 is at least partially outside a field of view of the camera 208. In some embodiments, the AI model 222 may include a plurality of submodules functioning in combination to execute the aforementioned steps for analyzing activity performance of the user. In an embodiment, the AI model 222 of the smart mirror 204 may include a recommendation engine for providing recommendations of activities based on performance data of the user 202. By way of an example, the performance data may include exercises performed, circuits performed, duration of exercises, activity performance, personal goals, user profile, age, weight, Body Mass Index (BMI), and the like.

As may be appreciated, the feedback based on the activity being performed by the user 102 may not be limited to instructions to perform corrective actions. The feedback may also include biometric feedback or warnings, for example, any irregularity or issues in one or more of pulse rate or heartbeat of the user 102, body temperature of the user 102, spasms in muscles, or pupil dilation, and other similar health issues. In some embodiments, feedback may be in the form of motivation or encouragement provided to the user 102 while performing the activity or after completion of the activity. By way of an example, in the form of audio feedback, messages like: "great job," "you are awesome," "great going," "perfectly done," "done like a pro," "you are the best," "that's the best I have seen," and other similar messages, may be provided to the user 102. The sound of clapping, cheers, or various exclamations may also be provided to the user 102 as feedback. These messages may also be provided in the form of visual feedback, such that, the messages may be displayed in textual form on the GUI of the smart mirror 100. Additionally, or alternatively, graphic elements, for example, bursting crackers, flying balloons, the sound of stadium crowd, or avatars of cheerleader, instructor, famous people (for example, Kai Greene, Phil Health, Ronnie Coleman, Arnold, and other famous personalities), may also be displayed to the user 102. In some configurations, gamification of the activities performed by the user and a rewarding mechanism may also be used as feedback provided to the user. As a result of such feedback, the user 102 may be constantly motivated and may not feel that he/she is performing any given activity in silo.

In some configurations, the user 102 may also be able to set goals related to various activities. In such case, the feedback may include status regarding percentage of goals achieved by the user 102.

In some embodiments, in order to provide feedback to the user 102 on their personal smart devices, i.e., third party smart devices, the smart mirror 100 may be configured with an open Application Programming Interface (API), which may enable such integration seamlessly. Moreover, data received from the third party smart devices may also be ingested into the smart mirror 100, via the open API, and may further be provided to the user 102 via the smart mirror 100 using visual elements (such as, graphs or charts), verbal and audio cues, or haptic cues. The data may also correspond to warnings and alerts generated by the third party smart devices. By way of an example, a smart watch that is configured to sense blood pressure of the user 102 may send data regarding the user 102 having high blood pressure to the smart mirror 100. Accordingly, the smart mirror 100 may render the message "Your blood pressure is too high, please relax and take a break" to the user 102, orally or visually. Thus, the smart mirror 100 may act as a collator of feedback and a single point smart device for viewing all feedbacks. In other words, since the smart mirror 100 generates feedback on its own and also receives feedback from other smart devices, the smart mirror 100 assimilates all feedback, refines it, and the presents it to the user 102 via the smart mirror. Thus, the user does not have to rely on multiple devices to receive various types of feedbacks.

Further, the user 102 may want to share activity performance with his friends on various social networks or with other remote users that may also use smart mirrors 100. To this end, the smart mirror 100 may be configured with various integrate with social media applications. Examples of these social media applications may include, but are not limited to FACEBOOK™, WHATSAPP™, YOUTUBE™, and/or INSTAGRAM™. In some embodiments, the smart mirror 100 may have these social media applications already installed therein. There may also be a social media application that is specific to the smart mirror 100 and is configured to only connect users of other smart mirrors 100 and/or display devices.

Thus, by way of integration with these social media applications, the user performance may be posted and published on one or more of these social media platforms and may be made available as online content for other users to access. The rewarding mechanism as discussed before may also be shared or used on social media platforms. In some configurations, scores related to user activities may be presented on a leader board as points for various users who use smart mirrors 100 and/or display devices. Badges may also be assigned to various users based on level of activities performed by them and may be displayed on social media platforms. Additionally, records related to exercises performed may also be displayed. Moreover, goals set by various users for activities and respective percentage completion of goals may also be displayed on social media platforms. As may be appreciated, feedback provided to users may also be shared within group of users on social media, including friends, social circles, and classes that may be connected in real-time.

The smart mirror 204 may continue to display the target activity performance as long as the current activity performance is in accordance with the target activity performance. However, when the current activity performance of the user 202, and target pose and the associated pose skeletal model, shows a deviation from the target activity performance of the activity expert, the smart mirror 204 may generate feedback for the user 202 to direct and instructor the user to ensure that the current activity performance is in accordance with the target activity performance. When the deviation of the current activity performance is above a predefined threshold performance and continues for a predefined threshold time, the smart mirror 204 may pause the display of the set of user performance parameters and the target activity performance.

In some embodiments, the smart mirror 204 may generate audio messages (such as, the number of reps in audio form, the aural feedback to the user 202, new achievements, personal best, messages from other users, advertising, challenges, errors, warnings, or the like) for the user 202 in an audio form via the speaker 212. It may be noted that when generating the audio messages, timing and duration of an audio output may be important. For example, when the user 202 is exercising at a high speed, some of the audio messages may become obsolete before generation. Moreover, some of the audio messages may become repetitive and unnatural. Additionally, some of the audio messages may be of a higher priority (for example, warnings and errors). In such scenarios, the audio messages may be generated through a mechanism based on priority queues. In an embodiment, the audio messages may use an AI-based approach to generate more natural dialogues. It may be noted that pose and exercise matching through AI may be performed on a remote server while recognition of key points may be performed on an edge node. Thus, transfer of heavy video data to the server can be avoided. Additionally, overall security may be enhanced since the pose and exercise matching is not known on an end edge device.

It should be noted that all such aforementioned modules 206-224 may be represented as a single module or a combination of different modules. Further, as will be appreciated by those skilled in the art, each of the modules 206-224 may reside, in whole or in parts, on one device or multiple devices in communication with each other. In some embodiments, each of the modules 206-224 may be implemented as dedicated hardware circuit comprising custom application-specific integrated circuit (ASIC) or gate arrays, off-the-shelf semiconductors such as logic chips, transistors, or other discrete components. Each of the modules 206-224 may also be implemented in a programmable hardware device such as a field programmable gate array (FPGA), programmable array logic, programmable logic device, and so forth. Alternatively, each of the modules 206-224 may be implemented in software for execution by various types of processors (e.g., processor 216). An identified module of executable code may, for instance, include one or more physical or logical blocks of computer instructions, which may, for instance, be organized as an object, procedure, function, or other construct. Nevertheless, the executables of an identified module or component need not be physically located together, but may include disparate instructions stored in different locations which, when joined logically together, include the module and achieve the stated purpose of the module. Indeed, a module of executable code could be a single instruction, or many instructions, and may even be distributed over several different code segments, among different applications, and across several memory devices over internet, cloud, and in parallel.

As will be appreciated by one skilled in the art, a variety of processes may be employed for analyzing activity performance of a user in real-time through a smart mirror. For example, the exemplary system 200 and the associated smart mirror 204 may analyze activity performance of a user in real-time by the processes discussed herein. In particular, as will be appreciated by those of ordinary skill in the art, control logic and/or automated routines for performing the techniques and steps described herein may be implemented by the system 200 and the associated smart mirror 204 either by hardware, software (such as, neural networks or other computational models), or combinations of hardware and software. For example, suitable code may be accessed and executed by the one or more processors on the smart mirror 204 to perform some or all of the techniques described herein. Similarly, application specific integrated circuits (ASICs) configured to perform some or all of the processes described herein may be included in the one or more processors on the smart mirror 204.

Figure 3A:
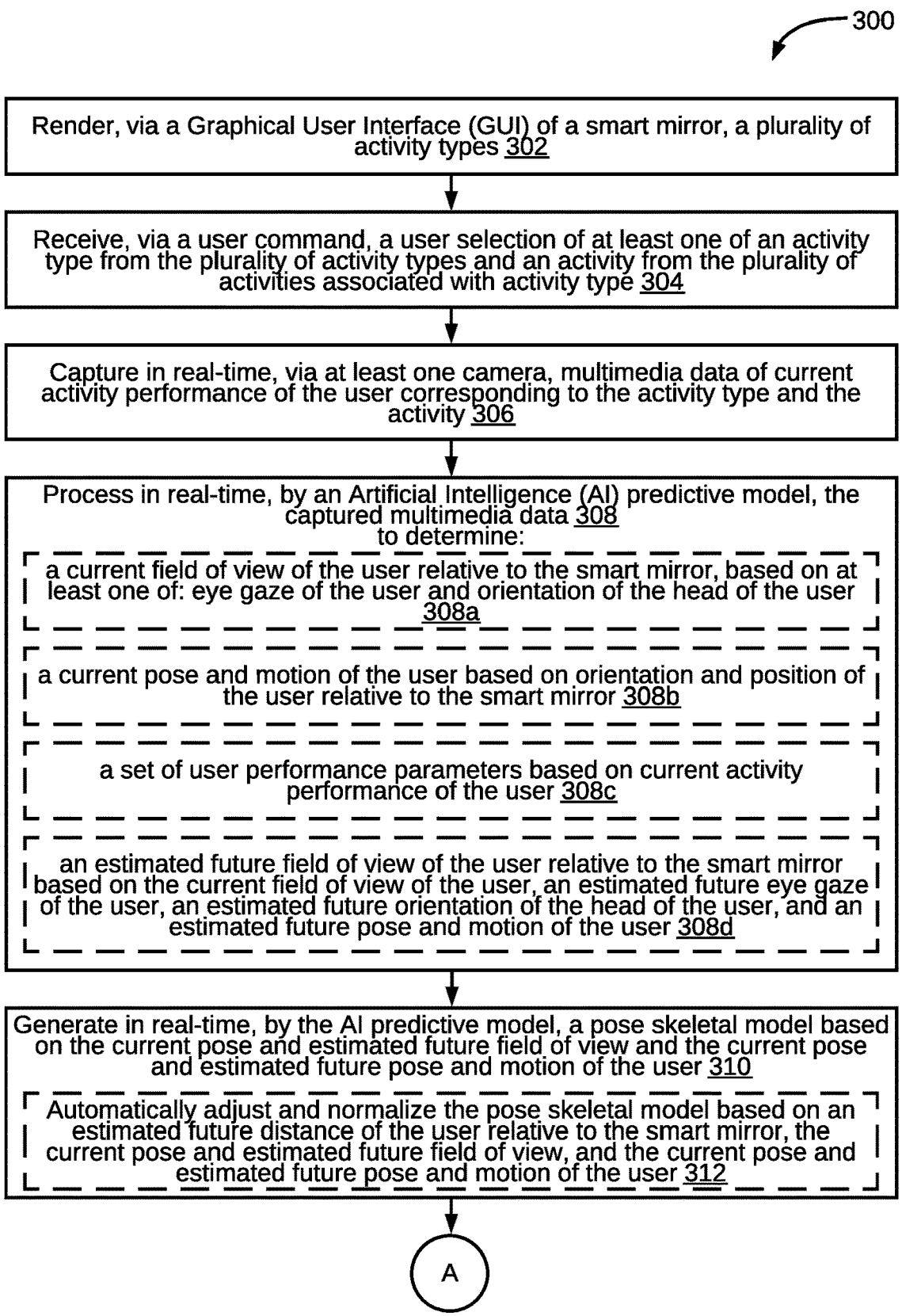
FIGS. 3A and 3B illustrate a flow diagram of an exemplary process for analysing activity performance of a user in real-time through a smart mirror, in accordance with some embodiments.
Figure 3B:
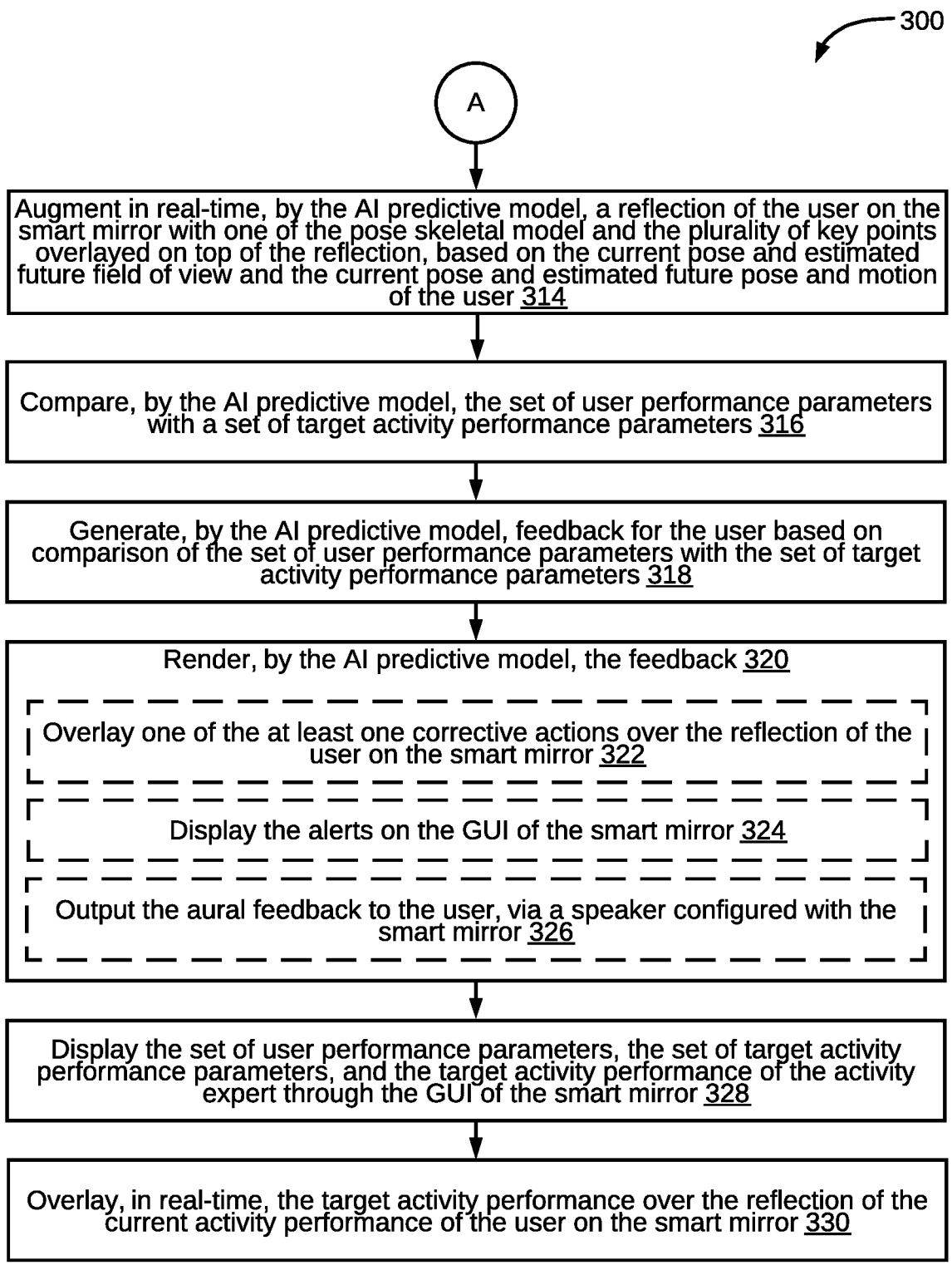

Referring now to FIGS. 3A and 3B, an exemplary process 300 for analyzing activity performance of a user in real-time through a smart mirror (for example, the smart mirror 100) is depicted via a flowchart, in accordance with some embodiments. In an embodiment, the process 300 may be implemented by the smart mirror 100 in the room 104. The process 300 includes rendering, via a Graphical User Interface (GUI) of a smart mirror, a plurality of activity types, at step 302. Each of the plurality activity types includes a plurality of activities. In an embodiment, the GUI may be rendered on the display 214 via the GUI module 220.

Further, the process 300 includes receiving, via a user command, a user selection of at least one of an activity type from the plurality of activity types and an activity from the plurality of activities associated with activity type, at step 304. The user command includes at least one of a voice command, a touch gesture, an air gesture, eye gesture, or a signal generated by an input device. In an embodiment, the voice command may be received by the microphone 210.

Further, the process 300 includes capturing in real-time, via at least one camera (for example, the at least one camera 108), multimedia data of current activity performance of the user corresponding to the activity type and the activity, at step 306. The multimedia data received from the at least one camera is stored in a database (such as, the database 224). In some embodiments, the user may edit the multimedia data based on one or more user commands. The user command is at least one of a text command, voice command, touch command, or a visual gesture. By way of an example, the one or more user commands include at least one of setting a start point of the multimedia data, setting an end point of the multimedia data, removing background from the multimedia data, assigning one or more tags to the multimedia data, and sharing the multimedia data with the activity expert or a set of other users. Alternately, the activity expert may record and edit multimedia data corresponding to the target activity performance to be shared with the user.

Further, the process 300 includes, at step 308, processing in real-time, by an AI model (such as, the AI model 222), the captured multimedia data to determine a current field of view of the user relative to the smart mirror (308a), a current pose and motion of the user (308b), a set of user performance parameters (308c), and an estimated future field of view of the user relative to the smart mirror (308d). The current field of view of the user relative to the smart mirror (308a) is determined based on at least one of: eye gaze of the user and orientation of the head of the user. The current pose and motion of the user (308b) is determined based on orientation and position of the user relative to the smart mirror. The set of user performance parameters (308c) is determined based on current activity performance of the user. The AI model is configured based on target activity performance of an activity expert, and a plurality of correct and incorrect movements associated with the current activity. The set of user performance parameters includes speed of the current activity performance, number of repetitions completed, overall completion of an activity circuit, third-party smart device information, pulse rate of the user, blood pressure of the user, and motion of the user. The estimated future field of view of the user relative to the smart mirror (308d) is determined based on the current field of view of the user, an estimated future eye gaze of the user, an estimated future orientation of the head of the user, and an estimated future pose and motion of the user.

Further, the process 300 includes generating in real-time, by the AI model, a pose skeletal model (for example, the pose skeletal model 116) based on the current pose and estimated future field of view and the current pose and estimated future pose and motion of the user, at step 310. The pose skeletal model includes a plurality of key points based on the activity type and the activity. Each of the plurality of key points is corresponds to a joint of the user. Further, the step 310 of the process 300 includes automatically adjusting and normalizing the pose skeletal model based on an estimated future distance of the user relative to the smart mirror, the current pose and estimated future field of view, and the current pose and estimated future pose and motion of the user, at step 312.

Further, the process 300 includes augmenting in real-time, by the AI model, a reflection of the user on the smart mirror with one of the pose skeletal model and the plurality of key points overlayed on top of the reflection, based on the current pose and estimated future field of view and the current pose and estimated future pose and motion of the user, at step 314. Each of the plurality of key points is overlayed over a corresponding joint or a feature of the user in the reflection.

Further, the process 300 includes comparing, by the AI model, the set of user performance parameters with a set of target activity performance parameters, at step 316. The set of target activity performance parameters corresponds to the activity expert. The set of target activity performance parameters includes speed of the target activity performance, target number of repetitions, target pulse rate of the user, and target motion of the user.

Further, the process 300 includes generating, by the AI model, feedback for the user based on comparison of the set of user performance parameters with the set of target activity performance parameters, at step 318. The feedback includes at least one of corrective actions or alerts. The feedback includes at least one of visual feedback, aural feedback, or haptic feedback. The feedback may include generating a warning to the user including indication for correcting the current pose of the user, indication for correcting user motion associated with the current pose of the user, and indication for correcting the current position of the user, when the user is at least partially outside a field of view of the at least one camera.

Further, the process 300 includes rendering, by the AI model, the feedback, at step 320. Further, the step 320 of the process 300 includes overlaying one of the at least one corrective actions over the reflection of the user on the smart mirror, at step 322. Further, the step 320 of the process 300 includes displaying the alerts on the GUI of the smart mirror, at step 324. Further, the step 320 of the process 300 includes outputting the aural feedback to the user, via a speaker configured with the smart mirror, at step 326.

In some embodiments, the process 300 includes pausing the display of the set of user performance parameters and the target activity performance when the current activity performance varies from the target activity performance above a predefined threshold performance for a predefined threshold time based on the comparing. Further, in such embodiments, the process 300 includes generating, by the AI model, feedback for the user based on comparison of the set of user performance parameters with the set of target activity performance parameters. It should be noted that the predefined threshold performance and the predefined threshold time are correlated. For example, even when the user is out of alignment from the target activity performance for a short time interval, the smart mirror 100 may pause the display. In some embodiments, the AI model dynamically determines values for each of the predefined threshold performance and the predefined threshold time based on user's skill level. In some embodiments, the AI model may use various parameters other than performance and time.

Further, the process 300 includes displaying the set of user performance parameters, the set of target activity performance parameters, and the target activity performance of the activity expert through the GUI of the smart mirror, at step 328. In an embodiment, multimedia data may be received from the activity expert corresponding to the target activity performance in real-time in response to the current activity performance of the user. In such an embodiment, the set of user performance parameters and the target activity performance of the activity expert are displayed in real-time through the GUI via the smart mirror. The target activity performance is overlayed over the reflection of the current activity performance of the user in real-time. Further, the process 300 includes overlaying, in real-time, the target activity performance over the reflection of the current activity performance of the user on the smart mirror, at step 330.

Figure 4:
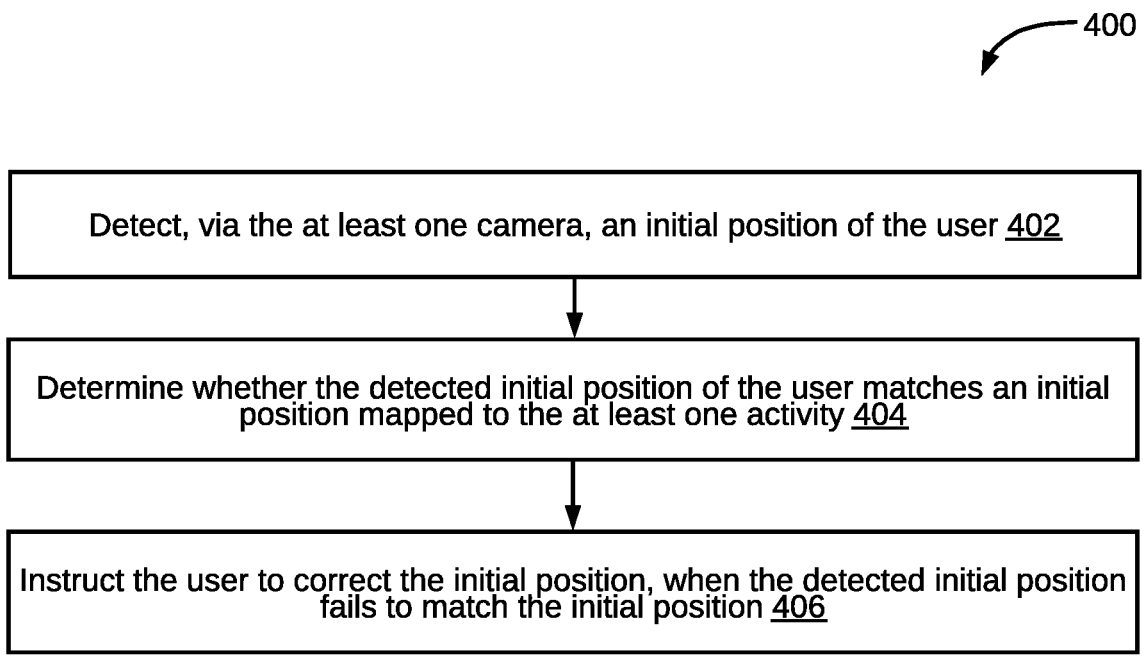

Referring now to FIG. 4, an exemplary process 400 for correcting initial position of a user is depicted via a flow chart, in accordance with some embodiments. In an embodiment, the process 400 is implemented by the smart mirror 100. The process 400 includes detecting, via the at least one camera, an initial position of the user, at step 402. Further, the process 400 includes determining whether the detected initial position of the user matches an initial position mapped to the at least one activity, at step 404. Further, the process 400 includes instructing the user to correct the initial position, when the detected initial position fails to match the initial position, at step 406. It may be noted that the steps 402-406 may be iteratively performed throughout the current activity performance of the user.

Figure 5:
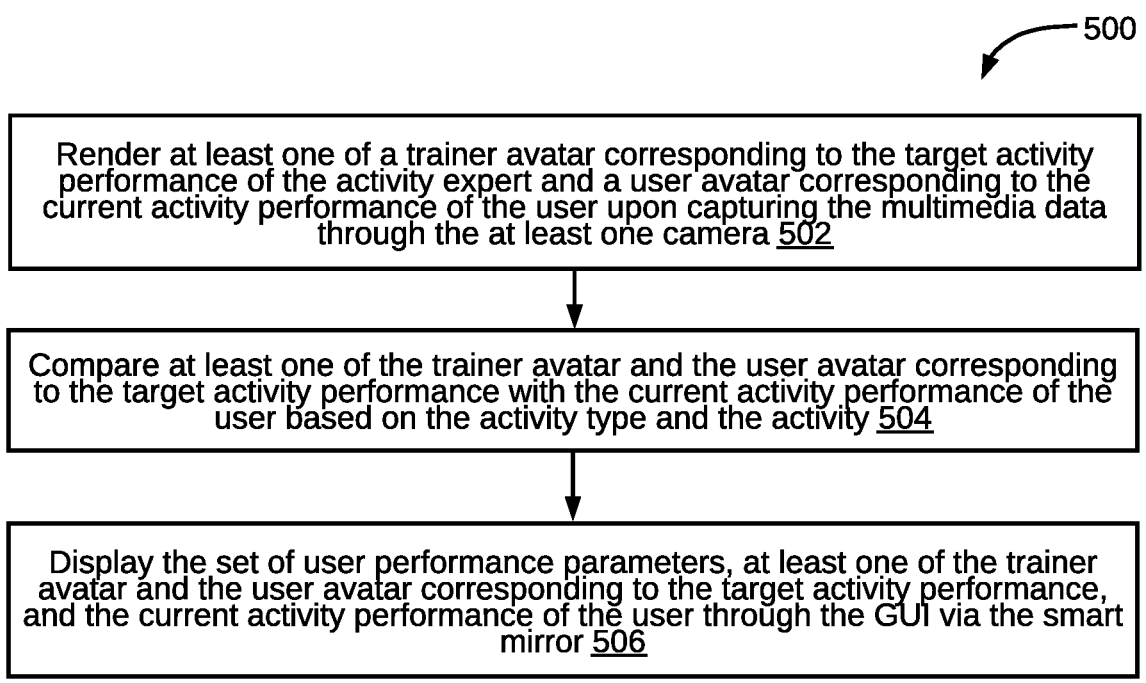

Referring now to FIG. 5, an exemplary process 500 for comparing trainer avatar corresponding to target activity performance with and user avatar corresponding to current activity performance of a user is depicted via a flow chart, in accordance with some embodiments. In an embodiment, the process 500 is implemented by the smart mirror 100. The process 500 includes rendering at least one of a trainer avatar corresponding to the target activity performance of the activity expert and a user avatar corresponding to the current activity performance of the user upon capturing the multimedia data through the at least one camera, at step 502. The trainer avatar is a 3D model of the activity expert and the user avatar is a multidimensional model of the user.

Further, the process 500 includes comparing at least one of the trainer avatar and the user avatar corresponding to the target activity performance with the current activity performance of the user based on the activity type and the activity, at step 504. Further, the process 500 includes displaying the set of user performance parameters, at least one of the trainer avatar and the user avatar corresponding to the target activity performance, and the current activity performance of the user through the GUI via the smart mirror, at step 506. The current activity performance is overlayed over at least one of the trainer avatar and the user avatar corresponding to the target activity performance in real-time. It may be noted that the steps 502-506 may be iteratively performed throughout the current activity performance of the user.

Figure 6:

Referring now to FIG. 6, an exemplary GUI 600 displaying a plurality of exercises 602 is illustrated, in accordance with some embodiments. By way of an example, the plurality of exercises 602 may include, but may not be limited to, lateral squat, lunges side, squat side, burpees side, pushups side, front triceps overhead, push-ups front, dumbbell squat press, squat front, and lunges front. Each of the plurality of exercises 602 may be, but may not be limited to, filtered based on a type of activity selected from a plurality of activity types 604. By way of an example, the plurality of activity types 604 may include, but may not be limited to, "arms", "chest", "lunges", "leg", "quads", "shoulder", "squats", and "triceps". The plurality of exercises 602 may be sorted based on one of the sorting criteria 606. By way of an example, the sorting criteria 606 may include, but may not be limited to, new exercises, latest exercises performed, most frequent exercises performed, and duration of an exercise. It may be noted that the GUI 600 may not be limited to fitness and may be customized based on user requirements and use cases. For example, the GUI 600 may include activities for specific therapies in case of rehab, meditations for Yoga, physiotherapy recommended by a medical professional, or the like.

Figure 7:
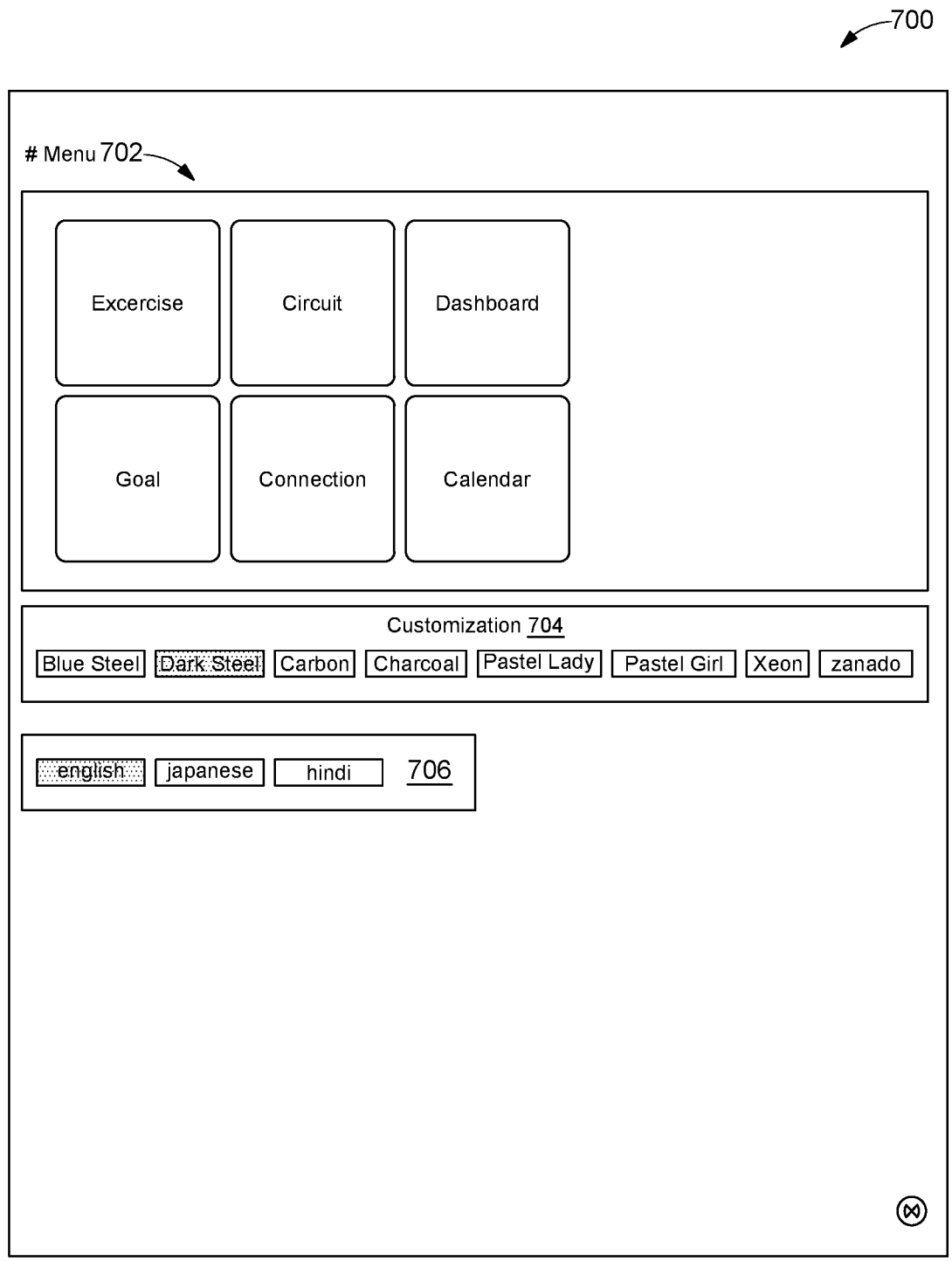

Referring now to FIG. 7, an exemplary GUI 700 displaying a home page of a fitness application is illustrated, in accordance with some embodiments. The GUI 700 may include a menu 702, customization 704, and a plurality of languages 706. By way of an example, the menu 702 may include, but may not be limited to, options for the user such as "exercise", "circuit", "dashboard", "goal", "connection", and "calendar". Further, the customization 704 may offer a choice for a theme color to the user. By way of an example, the theme color may be, but may not be limited to, blue steel, dark steel, carbon, charcoal, pastel lady, pastel girl, Xeon, and zanado. By way of an example, the plurality of languages 706 may include, but may not be limited to, English, Japanese, or Hindi.

Figure 8:
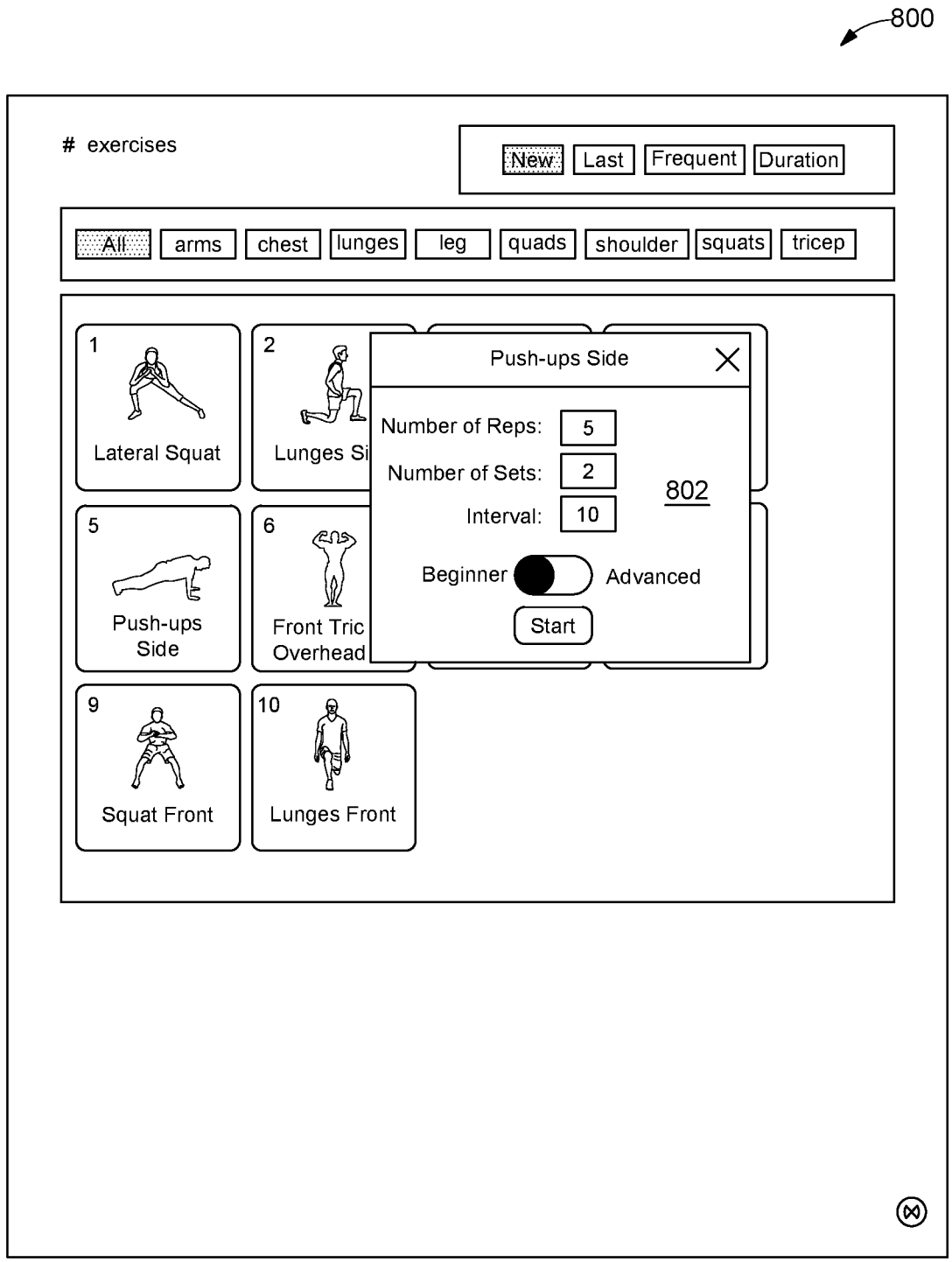

Referring now to FIG. 8, an exemplary GUI 800 displaying exercise parameters 802 is illustrated, in accordance with some embodiments. Upon receiving a user selection for an exercise, the GUI 800 may request the user for the exercise parameters 802. By way of an example, the exercise parameters 802 may include, but may not be limited to, number of reps, number of sets, interval, and a level of exercise (for example, beginner or advanced). In an embodiment, predefined parameter groups (such as, CROSSFIT®) maybe provided to the user.

Figure 9:
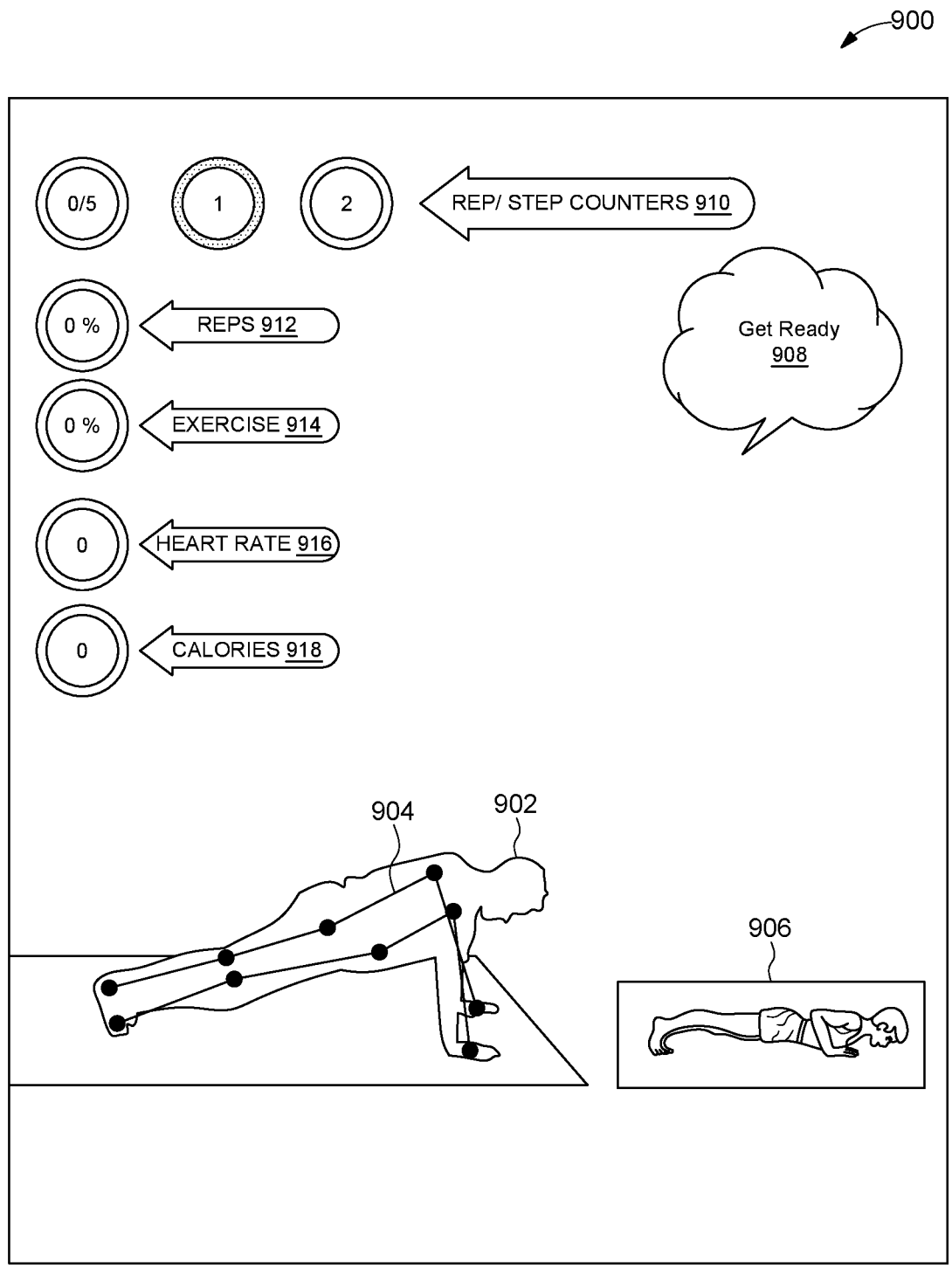

Referring now to FIG. 9, an exemplary GUI 900 displaying current activity performance 902 and pose skeletal model 904 of the user is illustrated, in accordance with some embodiments. In an embodiment, the GUI 900 may display the pose skeletal model 904 of the user overlayed upon the reflection of the user by the smart mirror (such as, the smart mirror 100). Further, the GUI 900 displays the target activity performance 906 corresponding to the activity expert in an inset frame on bottom right of display. Further, the GUI 900 displays a message 908 for the user to get ready for the exercise. The message 908 may also be provided as an audio output. Further, the GUI 900 displays a set of user performance parameters such as, but not limited to, rep/step counters 910, number of reps 912, exercise 914, heart rate 916, and calories 918. It should be noted that the rep/step counters 910 are a sequence of target poses in the target activity performance to be followed by the user.

Figure 10:
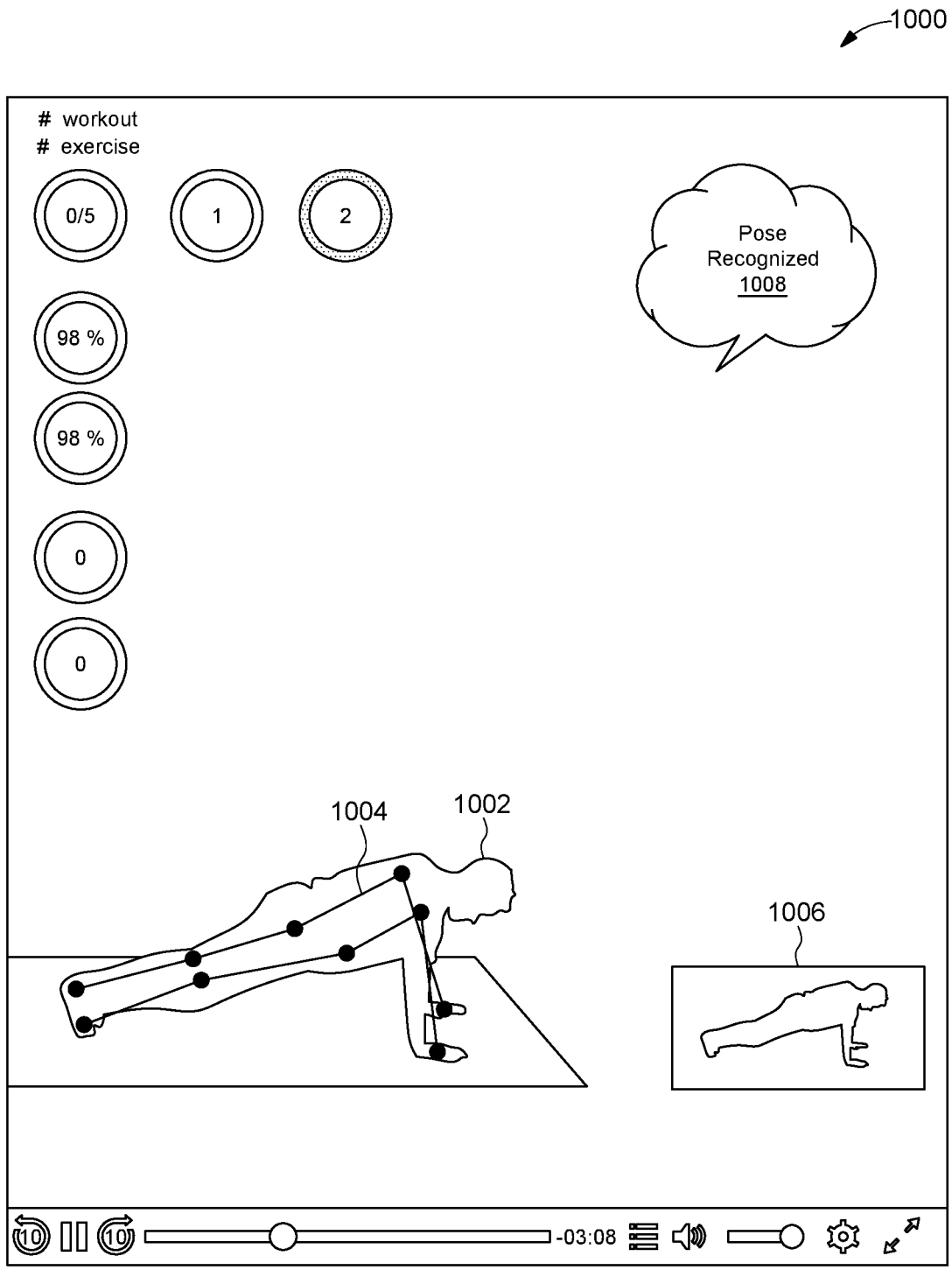

Referring now to FIG. 10, an exemplary GUI 1000 displaying current activity performance 1002 and pose skeletal model 1004 of a user is illustrated, in accordance with some embodiments. When the user acknowledges the message 908 and gets into an initial pose for the exercise, the AI model of the smart mirror (such as, the smart mirror 100) may determine whether the initial pose is correct. Further, the GUI 1000 displays a message 1008 for the user that the pose is recognized successfully for the exercise. The message 1008 may also be provided as an audio output. The user may be notified via text, graphic, visual, haptic, or audio output to begin the exercise. In an exemplary scenario, when the initial pose of the user is not correct, deviation from the target activity performance is presented to the user via a message (text, graphic, audio, visual, or haptic).

Figure 11:
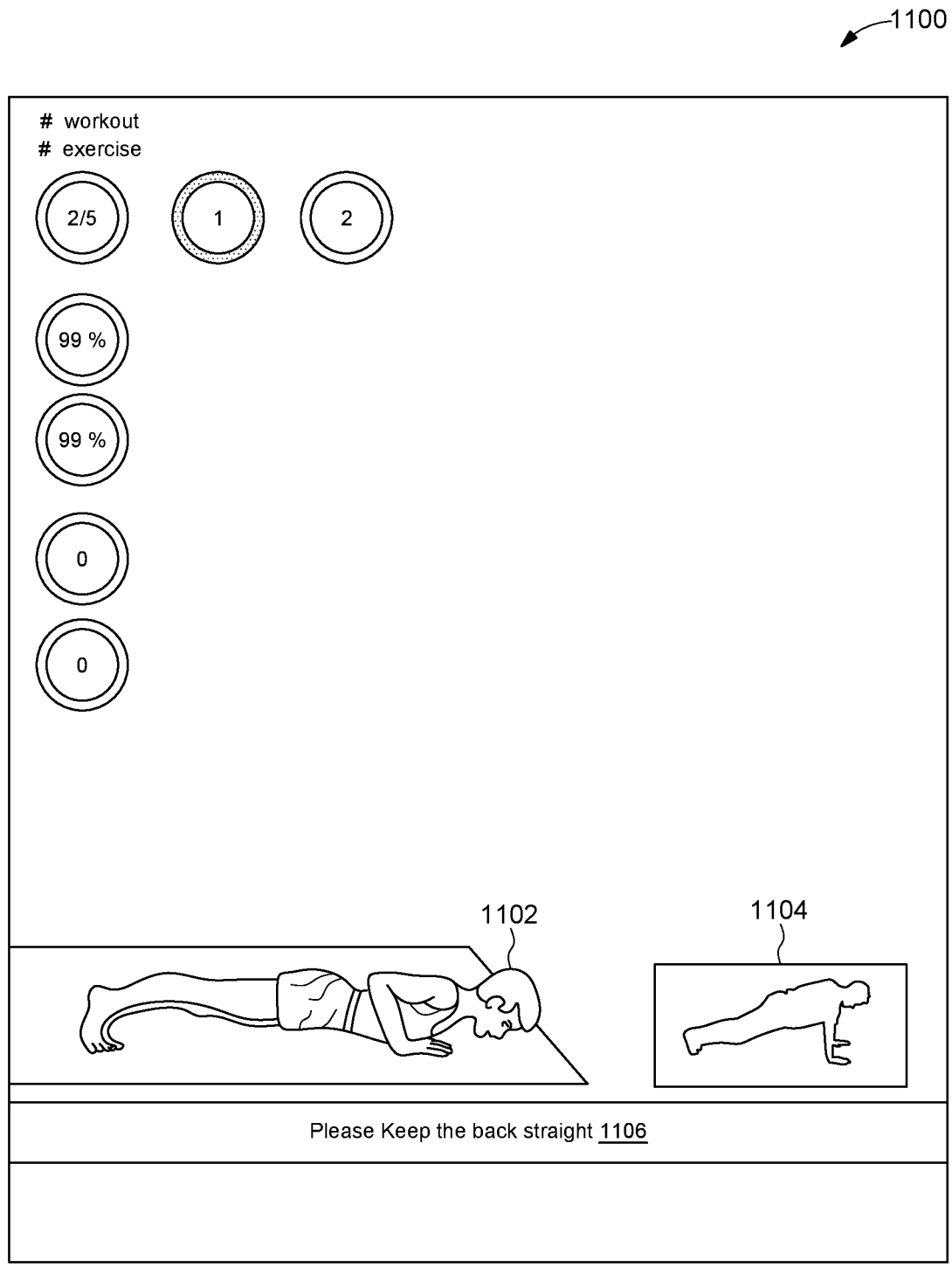

Referring now to FIG. 11, an exemplary GUI 1100 displaying current activity performance 1102 of the user is illustrated, in accordance with some embodiments. When the user begins performing the exercise, the multimedia data associated with the current activity performance 1102 of the user is analyzed by the AI model of the smart mirror (such as, the smart mirror 100). The multimedia data of the current activity performance 1102 is compared with a target activity performance 1104 of the activity expert. By way of an example, the GUI 1100 may display rep/step counters, percentage of reps completed, percentage of exercise completed, heart rate of the user, calories burnt by the user, or any other user performance parameter. When the user successfully moves from an initial pose to a subsequent pose, the rep/step counter will change in value from "1" to "2", denoting that the user is now on second step. It should be noted that many activities have multiple steps. For example, a rep of burpees has 8 steps. When the current activity performance 1102 deviates from the target activity performance 1104 above a predefined threshold performance, a message 1106 is displayed on the display with a corrective action for the user (for example, "please keep your back straight"). The message 1106 may also be provided as an audio output and graphic indication. Further, the target activity performance 1104 of the activity expert is displayed for the user to follow with the current activity performance 1102.

Some embodiments of the present disclosure may be employed in a gymnasium, rehab, physiotherapy inside a hospital, dance studios, theatre, or any other use case scenario. The gymnasium may include, for example, multiple exercise machines and equipment for performing multiple activities by the user. The user may use a smart mirror (for example, the smart mirror 100) or any other display device to select an activity from the activity categories and may correspondingly select an activity attribute that is associated the activity. The multiple cameras may capture the activity of the user and may provide relevant instructions and feedback to the user for improvising the activities being performed. The cameras may also be used for facial recognition of the users to identify the users and provide history, customized settings, messages from trainers, profile data, and other similar information to the users. In a gymnasium, a single smart mirror may include multiple screens and GUIs positioned behind the one-way mirror to provide exercise training to a plurality of users. Further, the smart mirror 100 is configured to output audio feedback via a Bluetooth headset or speaker.

The cameras may be used to track and record the activity of the user in the gymnasium as the user moves from one area or from one machine to another for performing various activities. The smart mirror 100 may track current progress of the user using the cameras as the user moves from one area of the gymnasium to another. The cameras may allow continuity of the user's context and information across the monitor. The gymnasium (or any other use case scenario) may have various types of activity experts, such as personal coaches, trainers, gym activity experts, physical therapist, occupational therapist, physical education teachers, martial arts teachers, dance and choreography, sports personalities, team coach, and demonstrators and other trainers in health and fitness.

The activities performed in the gymnasium and the goals achieved by the user may be shared by the activity expert or the user with one or more other users practicing in the gymnasium or with one or more remote users.

In addition, the user performance may be posted and published on social media platforms and may be made available as online content for the one or more remote users to access. This may be done via gamification of the activities performed by the user and using a rewarding mechanism. Scores related to user activities may be presented on a leader board as points. Badges may be assigned to the user based on level of activities performed. In addition, records related to activities performed that may include, for example, accuracy, total count of exercises performed, breaks between the exercises, and the like, may be provided to the one or more users and may also be displayed on the display devices and smart mirrors. Further, the smart mirror 100 may include additional features such as unlocking features, additional activities, designs, and other similar features.

In an embodiment, the smart mirror 100 may be used to create content media and may share the content media comprising information related to, for example, current health status of the user, exercising routine, exercising capacity and previous records and earned rewards for the user on social media platforms. This may be done through an application programming interface (API) integrated with the smart mirror 100.

The smart mirror 100 may be used as a recording tool for creating new fitness content and associated instructions for the activity to be performed by the user as received through voice based input. Further, both the display device and smart mirror as used in the gymnasium (or any other use case scenario) may be used for editing and reviewing new content related to activities being selected by the user and may be used for reviewing the user's session by the activity expert. In addition, the smart mirror 100 may be connected to a health and fitness application using which the users may log into the smart mirror 100. Feedback as received on the health and fitness application may be shared on the social platforms for social engagement and provide activity related data to other socially connected parties or groups in form of leaderboards.

Further, the smart mirror 100 may be used as a recording device by the user or the activity expert. As may be appreciated, the user and the activity expert using the smart mirror 100 may crop, highlight, add voice, voice-to-text feedback on the smart mirror. Additionally, the user and the activity expert may be permitted to add or remove background image as used in the smart mirror. The recorded videos may be shared with other users. Additionally, the parameters collected by the smart mirror may be processed to create metadata, instructions, threshold parameters, and combinations thereof.

The smart mirror 100 may use the one or more cameras and other one or more sensors to capture position of the user during performing the activity. The feedback based on the activity being performed by the user is not limited to instructions related to slowing down visual and other media components, such as a video of the target motion, but may also include other feedback such as beats and rhythm audio cues, such as a metronome. For generating correct and timely feedback, a tight coupling of movement of the user may be done to provided performance guidance clues, target movements, media and voice and audio feedback. The smart mirror 100 may map and synchronize media and information as provided with actual movement of the user and may thus provide relevant corresponding feedback.

In an embodiment, a multi-language voice based interface may be provided for enabling the user to navigate, select, schedule and sequence an activity from the plurality of activity categories. The voice based input may be used to create and save playlists, add metadata to the playlists, add comments using speech-to-text mechanism and audio feedback to the playlists and the activities, record a new activity category, edit and clip the activity to be performed, tag an exercise with hashtags, for example, type of exercise, muscle groups or level of difficulty, replace an exercise clip with an alternative version, share playlists and exercises with other users, dictate a message for another user when sharing the playlists.

Some embodiments of the present disclosure may be implemented as an AI-based health and fitness system training method. The method includes detecting a user, determining pose and body movement of a user using a camera, further sensing motion, position, and/or movement of the body or user using a sensor(s), directing and monitoring the exercise through the pose determination and the body movement of the user on the smart mirror, overlaying the pose and the movement over a mirror reflection of the user and providing real time feedback, overlaying the pose over a video stream of an activity expert and showing the pose position in conjunction with the training video and user, tracking exercise in real time, automatic rep counting, guiding and target correlation and accuracy in an exercise sequence and real time social media sharing to groups, friends and others.

In an alternate embodiment, the Artificial Intelligence based health and fitness training method, includes a camera for determining pose and body movement of a user; a microphone for listening for the user's voice instructions; a speaker for providing feedback to the user on their movements, whereby the method provides for determining the pose and the body movement of the user to track exercise in real time, for automatic rep counting, to guide and target correlation in an exercise sequence.

In an embodiment, real-time live feedback may be provided using voice controlled instructions, visuals including video or textual or graphic elements based on instructions for the exercise, scripts, sequence of the exercise and/or performance of the user during performing the activity. The smart mirror 100 may include information related to, for example, details related to user's account access, user's workout history and other information relevant information related to the user. The smart mirror 100 may determine pose and body movement of the user, overlaying pose and movement of the user over a mirror refection of the user and also overlaying the pose over a video stream of the activity expert and showing the pose position in conjunction with the training video and the user. Based on the AI model, the smart mirror 100 may provide live feedback to the user based on instructions related to, for example, exercise/activity, scripts, sequence of the exercise and/or performance of the user during exercise through audio feedback/video feedback/textual feedback/graphic feedback.

In an embodiment, for efficient display of the guidance steps and placement of visual information related to the guidance steps may be presented on a screen of the smart mirror. The smart mirror GUI may be adjusted based on eye position of the user so that the information is placed appropriate to reflection rather than capture of video stream of the user or in some fixed position.

Further, a 3D model of pose and movement of the user on the smart mirror is provided. This is accompanied by overlaying the provided 3D model over reflection and then the 3D model may be rendered along with analysis for display through the smart mirror. As may be appreciated, the one or more cameras capturing the user's pose and motion mid-way along the long side of the mirror may be adjusted for allowing a better aspect ratio of the user's pose.

The video recording may be created using at least one camera placed at distributed locations. The smart mirror 100 may include a recording device for creating new training content, for recording content to be reviewed later by an activity expert, physiotherapist, teacher, choreographer and for real-time sharing of the activity expert's or user's live stream.

As will be also appreciated, the above described techniques may take the form of computer or controller implemented processes and apparatuses for practicing those processes. The disclosure can also be embodied in the form of computer program code containing instructions embodied in tangible media, such as floppy diskettes, solid state drives, CD-ROMs, hard drives, or any other computer-readable storage medium, wherein, when the computer program code is loaded into and executed by a computer or controller, the computer becomes an apparatus for practicing the invention. The disclosure may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

Figure 12:
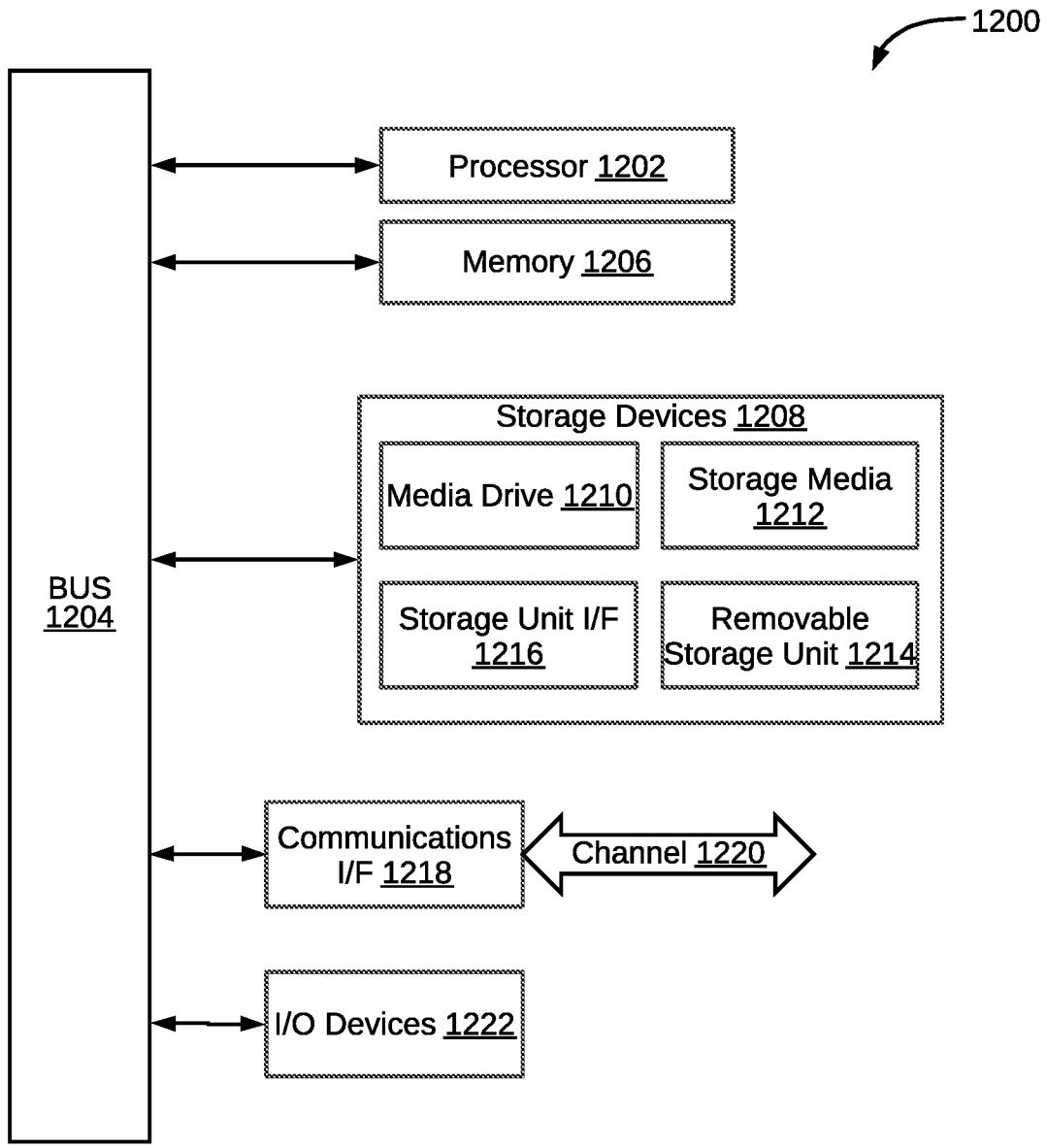
FIG. 12 is a block diagram of an exemplary computer system for implementing embodiments consistent with the present disclosure.

The disclosed methods and systems may be implemented on a conventional or a general-purpose computer system, such as a personal computer (PC) or server computer. Referring now to FIG. 12, an exemplary computing system 1200 that may be employed to implement processing functionality for various embodiments (e.g., as a SIMD device, client device, server device, one or more processors, or the like) is illustrated. Those skilled in the relevant art will also recognize how to implement the invention using other computer systems or architectures. The computing system 1200 may represent, for example, a user device such as a desktop, a laptop, a mobile phone, personal entertainment device, DVR, and so on, or any other type of special or general-purpose computing device as may be desirable or appropriate for a given application or environment. The computing system 1200 may include one or more processors, such as a processor 1202 that may be implemented using a general or special purpose processing engine such as, for example, a microprocessor, microcontroller or other control logic. In this example, the processor 1202 is connected to a bus 1204 or other communication medium. In some embodiments, the processor 1202 may be an Artificial Intelligence (AI) processor, which may be implemented as a Tensor Processing Unit (TPU), or a graphical processor unit, or a custom programmable solution Field-Programmable Gate Array (FPGA).

The computing system 1200 may also include a memory 1206 (main memory), for example, Random Access Memory (RAM) or other dynamic memory, for storing information and instructions to be executed by the processor 1202. The memory 1206 also may be used for storing temporary variables or other intermediate information during execution of instructions to be executed by the processor 1202. The computing system 1200 may likewise include a read only memory ("ROM") or other static storage device coupled to bus 1204 for storing static information and instructions for the processor 1202.

The computing system 1200 may also include a storage devices 1208, which may include, for example, a media drive 1210 and a removable storage interface. The media drive 1210 may include a drive or other mechanism to support fixed or removable storage media, such as a hard disk drive, a floppy disk drive, a magnetic tape drive, an SD card port, a USB port, a micro USB, an optical disk drive, a CD or DVD drive (R or RW), or other removable or fixed media drive. A storage media 1212 may include, for example, a hard disk, magnetic tape, flash drive, or other fixed or removable medium that is read by and written to by the media drive 1210. As these examples illustrate, the storage media 1212 may include a computer-readable storage medium having stored therein particular computer software or data.

In alternative embodiments, the storage devices 1208 may include other similar instrumentalities for allowing computer programs or other instructions or data to be loaded into the computing system 1200. Such instrumentalities may include, for example, a removable storage unit 1214 and a storage unit interface 1216, such as a program cartridge and cartridge interface, a removable memory (for example, a flash memory or other removable memory module) and memory slot, and other removable storage units and interfaces that allow software and data to be transferred from the removable storage unit 1214 to the computing system 1200.

The computing system 1200 may also include a communications interface 1218. The communications interface 1218 may be used to allow software and data to be transferred between the computing system 1200 and external devices. Examples of the communications interface 1218 may include a network interface (such as an Ethernet or other NIC card), a communications port (such as for example, a USB port, a micro USB port), Near field Communication (NFC), and other similar communication interfaces. Software and data transferred via the communications interface 1218 are in the form of signals which may be electronic, electromagnetic, optical, or other signals capable of being received by the communications interface 1218. These signals are provided to the communications interface 1218 via a channel 1220. The channel 1220 may carry signals and may be implemented using a wireless medium, wire or cable, fiber optics, or other communications medium. Some examples of the channel 1220 may include a phone line, a cellular phone link, an RF link, a Bluetooth link, a network interface, a local or wide area network, and other communications channels.

The computing system 1200 may further include Input/Output (I/O) devices 1222. Examples may include, but are not limited to a display, keypad, microphone, audio speakers, vibrating motor, LED lights, and other similar I/O devices. The I/O devices 1222 may receive input from a user and also display an output of the computation performed by the processor 1202. In this document, the terms "computer program product" and "computer-readable medium" may be used generally to refer to media such as, for example, the memory 1206, the storage devices 1208, the removable storage unit 1214, or signal(s) on the channel 1220. These and other forms of computer-readable media may be involved in providing one or more sequences of one or more instructions to the processor 1202 for execution. Such instructions, generally referred to as "computer program code" (which may be grouped in the form of computer programs or other groupings), when executed, enable the computing system 1200 to perform features or functions of embodiments of the present invention.

In an embodiment where the elements are implemented using software, the software may be stored in a computer-readable medium and loaded into the computing system 1200 using, for example, the removable storage unit 1214, the media drive 1210 or the communications interface 1218. The control logic (in this example, software instructions or computer program code), when executed by the processor 1202, causes the processor 1202 to perform the functions of the invention as described herein.

As will be appreciated by those skilled in the art, the techniques described in the various embodiments discussed above are not routine, or conventional, or well understood in the art. The techniques discussed above provide for analyzing activity performance of a user in real-time through a smart mirror. The techniques first render a plurality of activity types via a GUI. Each of the plurality activity types includes a plurality of activities. The techniques may then receive, via a user command, a user selection of at least one of an activity type from the plurality of activity types and an activity from the plurality of activities associated with activity type. The techniques may then capture in real-time multimedia data of current activity performance of the user corresponding to the activity type and the activity. The techniques may then process in real-time, by an AI model, the captured multimedia data to determine a current field of view of the user relative to the smart mirror, based on at least one of: eye gaze of the user and orientation of the head of the user; a current pose and motion of the user based on orientation and position of the user relative to the smart mirror; a set of user performance parameters based on current activity performance of the user, wherein the AI model is configured based on target activity performance of an activity expert, and a plurality of correct and incorrect movements associated with the current activity; and an estimated future field of view of the user relative to the smart mirror based on the current field of view of the user, an estimated future eye gaze of the user, an estimated future orientation of the head of the user, and an estimated future pose and motion of the user. The techniques may then generate in real-time, by the AI model, a pose skeletal model based on the current pose and estimated future field of view and the current pose and estimated future pose and motion of the user. The pose skeletal model includes a plurality of key points based on the activity type and the activity. Each of the plurality of key points corresponds to a joint of the user. The techniques may then augment in real-time, by the AI model, a reflection of the user on the smart mirror with one of the pose skeletal model and the plurality of key points overlayed on top of the reflection, based on the current pose and estimated future field of view and the current pose and estimated future pose and motion of the user. Each of the plurality of key points is overlayed over a corresponding joint of the user in the reflection. The techniques may then compare, by the AI model, the set of user performance parameters with a set of target activity performance parameters. The set of target activity performance parameters corresponds to the activity expert. The techniques may then generate, by the AI model, feedback for the user based on comparison of the set of user performance parameters with the set of target activity performance parameters. The feedback includes at least one of corrective actions or alerts. The feedback includes at least one of visual feedback, aural feedback, or haptic feedback. The techniques may then render, by the AI model, the feedback. To render the feedback, the techniques may then overlay one of the at least one corrective actions over the reflection of the user on the smart mirror. To render the feedback, techniques may then display the alerts on the GUI of the smart mirror. To render the feedback, the techniques may then output the aural feedback to the user, via a speaker configured with the smart mirror.

In light of the above mentioned advantages and the technical advancements provided by the disclosed method and system, the claimed steps as discussed above are not routine, conventional, or well understood in the art, as the claimed steps enable the following solutions to the existing problems in conventional technologies. Further, the claimed steps clearly bring an improvement in the functioning of the device itself as the claimed steps provide a technical solution to a technical problem.

The specification has described method and system for analyzing activity performance of a user in real-time through a smart mirror. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, and/or deviations of those described herein) will be apparent to persons skilled in the relevant art(s) based on the teachings contained herein. Such alternatives fall within the scope and spirit of the disclosed embodiments.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for analyzing activity performance of a user in real-time through a smart mirror, the method comprising:
   rendering, via a Graphical User Interface (GUI) of a smart mirror, a plurality of activity types, wherein each of the plurality activity types comprises a plurality of activities;
   receiving, via a user command, a user selection of at least one of an activity type from the plurality of activity types and an activity from the plurality of activities associated with the activity type;
   capturing in real-time, via at least one camera, multimedia data of current activity performance of the user corresponding to the activity type and the activity;
   processing in real-time, by an Artificial Intelligence (AI) model, the captured multimedia data to determine:
      a current field of view of the user relative to the smart mirror, based on at least one of: eye gaze of the user and orientation of the head of the user;
      a current pose and motion of the user based on orientation and position of the user relative to the smart mirror;
      a set of user performance parameters based on current activity performance of the user, wherein the AI model is configured based on target activity performance of an activity expert, and a plurality of correct and incorrect movements associated with the activity; and
      an estimated future field of view of the user relative to the smart mirror based on the current field of view of the user, an estimated future eye gaze of the user, an estimated future orientation of the head of the user, and an estimated future pose and motion of the user;
   generating in real-time, by the AI model, a pose skeletal model based on the estimated future field of view and the current pose and estimated future pose and motion of the user, wherein the pose skeletal model comprises a plurality of key points based on the activity type and the activity, and wherein each of the plurality of key points corresponds to a joint or a feature of the user;
   augmenting in real-time, by the AI model, a reflection of the user on the smart mirror with the pose skeletal model overlaid on top of the reflection, based on the estimated future field of view and the current pose and estimated future pose and motion of the user, and wherein each of the plurality of key points of the pose skeletal model is overlaid over a corresponding joint of the user in the reflection;
   comparing, by the AI model, the set of user performance parameters with a set of target activity performance parameters, wherein the set of target activity performance parameters corresponds to the activity expert;
   generating, by the AI model, feedback for the user based on the comparison of the set of user performance parameters with the set of target activity performance parameters, wherein the feedback comprises at least one of corrective actions or alerts, and wherein the feedback comprises at least one of visual feedback, aural feedback, or haptic feedback; and
   rendering, by the AI model, the feedback, wherein rendering the feedback comprises:
      overlaying the corrective actions over the reflection of the user on the smart mirror;
      displaying the alerts on the GUI of the smart mirror; and
      outputting the aural feedback to the user, via a speaker configured with the smart mirror.

2. The method of claim 1, wherein generating the pose skeletal model comprises:
   automatically adjusting and normalizing the pose skeletal model based on an estimated future distance of the user relative to the smart mirror, the estimated future field of view, and the current pose and estimated future pose and motion of the user.

3. The method of claim 2, wherein the feedback comprises generating a warning to the user comprising:
   indication for correcting the current pose of the user;
   indication for correcting user motion associated with the current pose of the user; and
   indication for correcting the current position of the user, when the user is at least partially outside a field of view of the at least one camera.

4. The method of claim 1, further comprising displaying the set of user performance parameters, the set of target activity performance parameters, and the target activity performance of the activity expert through the GUI of the smart mirror.

5. The method of claim 4, further comprising overlaying, in real-time, the target activity performance over the reflection of the current activity performance of the user on the smart mirror.

6. The method of claim 4, further comprising:
pausing the display of the set of user performance parameters and the target activity performance when the current activity performance varies from the target activity performance above a predefined threshold performance for a predefined threshold time based on the comparing; and
generating, by the AI model, feedback for the user based on the comparison of the set of user performance parameters with the set of target activity performance parameters.

7. The method of claim 1, wherein the set of user performance parameters comprises speed of the current activity performance, number of repetitions completed, overall completion of an activity circuit, third-party smart device information, pulse rate of the user, blood pressure of the user, and motion of the user, and wherein the set of target activity performance parameters comprises speed of the target activity performance, target number of repetitions, target pulse rate of the user, and target motion of the user.

8. The method of claim 1, further comprising:
rendering at least one of a trainer avatar corresponding to the target activity performance of the activity expert and a user avatar corresponding to the current activity performance of the user upon capturing the multimedia data through the at least one camera, wherein the trainer avatar is a 3-Dimensional (3D) model of the activity expert, and the user avatar is a multidimensional model of the user.

9. The method of claim 8, further comprising:
comparing at least one of the trainer avatar corresponding to the target activity performance with the user avatar corresponding to the current activity performance of the user based on the activity type and the activity; and
displaying the set of user performance parameters, at least one of the trainer avatar corresponding to the target activity performance, and the user avatar corresponding to the current activity performance of the user through the GUI via the smart mirror, wherein the current activity performance is overlaid over at least one of the trainer avatar and the user avatar in real-time.

10. The method of claim 1, further comprising:
storing the multimedia data received from the at least one camera in a database; and
editing the multimedia data based on one or more user commands received from the user, wherein the user command is at least one of a text command, voice command, touch command, or a visual gesture, wherein the one or more user commands comprise at least one of:
setting a start point of the multimedia data;
setting an end point of the multimedia data;
removing background from the multimedia data;
assigning one or more tags to the multimedia data; and
sharing the multimedia data with a set of other users.

11. The method of claim 1, further comprising:
receiving multimedia data from the activity expert corresponding to the target activity performance in real-time in response to the current activity performance of the user; and displaying the set of user performance parameters and the target activity performance of the activity expert in real-time through the GUI via the smart mirror, wherein the target activity performance is overlaid over the reflection of the current activity performance of the user in real-time.

12. The method of claim 1, further comprising:
detecting, via the at least one camera, an initial position of the user;
determining whether the detected initial position of the user matches an initial position mapped to the activity from the plurality of activities; and
instructing the user to correct the initial position, when the detected initial position fails to match the initial position.

13. The method of claim 1, wherein the user command comprises at least one of a voice command, a touch gesture, an air gesture, eye gesture, or a signal generated by an input device.

14. A smart mirror for analyzing activity performance of a user in real-time through a smart mirror, the smart mirror comprising:
a one-way mirror;
a display coupled with the one-way mirror, the display comprising a Graphical User Interface (GUI), wherein the GUI is configured to:
render a plurality of activity types, wherein each of the plurality of activity types comprises a plurality of activities;
receive, via a user command, a user selection of at least one of an activity type from the plurality of activity types and an activity from the plurality of activities associated with the activity type;
at least one camera configured to capture in real-time multimedia data of current activity performance of the user corresponding to the activity type and the activity;
a processor; and
a memory communicatively coupled to the processor, wherein the memory stores processor instructions, which when executed by the processor, cause the processor to:
process in real-time, by an Artificial Intelligence (AI) model, the captured multimedia data to determine:
a current field of view of the user relative to the smart mirror, based on at least one of: eye gaze of the user and orientation of the head of the user;
a current pose and motion of the user based on orientation and position of the user relative to the smart mirror;
a set of user performance parameters based on current activity performance of the user, wherein the AI model is configured based on target activity performance of an activity expert, and a plurality of correct and incorrect movements associated with the activity; and
an estimated future field of view of the user relative to the smart mirror based on the current field of view of the user, an estimated future eye gaze of the user, an estimated future orientation of the head of the user, and an estimated future pose and motion of the user;
generate in real-time, by the AI model, a pose skeletal model based on the estimated future field of view and the current pose and estimated future pose and motion of the user, wherein the pose skeletal model comprises a plurality of key points based on the activity type and the activity, and wherein each of the plurality of key points corresponds to a joint of the user;

augment in real-time, by the AI model, a reflection of the user on the smart mirror with the pose skeletal model overlaid on top of the reflection, based on the estimated future field of view and the current pose and estimated future pose and motion of the user, and wherein each of the plurality of key points of the pose skeletal model is overlaid over a corresponding joint of the user in the reflection;

compare, by the AI model, the set of user performance parameters with a set of target activity performance parameters, wherein the set of target activity performance parameters corresponds to the activity expert;

generate, by the AI model, feedback for the user based on the comparison of the set of user performance parameters with the set of target activity performance parameters, wherein the feedback comprises at least one of corrective actions or alerts, and wherein the feedback comprises at least one of visual feedback, aural feedback, or haptic feedback; and render, by the AI model, the feedback, wherein rendering the feedback comprises:
overlaying the corrective actions over the reflection of the user on the smart mirror;
displaying the alerts on the GUI of the smart mirror; and
outputting the aural feedback to the user, via a speaker configured with the smart mirror.

15. The smart mirror of claim 14, wherein to generate the pose skeletal model, the processor instructions, on execution, cause the processor to:
automatically adjust and normalize the pose skeletal model based on an estimated future distance of the user relative to the smart mirror, the current pose, the estimated future field of view, and the estimated future pose and motion of the user, wherein the feedback comprises generating a warning to the user comprising:
indication for correcting the current pose of the user;
indication for correcting user motion associated with the current pose of the user; and
indication for correcting the current position of the user, when the user is at least partially outside a field of view of the at least one camera.

16. The smart mirror of claim 14, wherein the processor instructions, on execution, further cause the processor to:
display the set of user performance parameters, the set of target activity performance parameters, and the target activity performance of the activity expert; and
overlay, in real-time, the target activity performance over the reflection of the current activity performance of the user on the smart mirror.

17. The smart mirror of claim 14, wherein the processor instructions, on execution, further cause the processor to:
render at least one of a trainer avatar corresponding to the target activity performance of the activity expert and a user avatar corresponding to the current activity performance of the user upon capturing the multimedia data through the at least one camera, wherein the trainer avatar is a 3-Dimensional (3D) model of the activity expert and the user avatar is a multidimensional model of the user;
compare at least one of the trainer avatar corresponding to the target activity performance with the user avatar corresponding the current activity performance of the user based on the activity type and the activity; and
display the set of user performance parameters, at least one of the trainer avatar corresponding to the target activity performance, and the user avatar corresponding to the current activity performance of the user through the GUI via the smart mirror, wherein the current activity performance is overlaid over at least one of the trainer avatar and the user avatar in real-time.

18. The smart mirror of claim 14, wherein the processor instructions, on execution, further cause the processor to:
store the multimedia data received from the at least one camera in a database; and
edit the multimedia data based on one or more user commands received from the user, wherein the user command is at least one of a text command, voice command, touch command, or a visual gesture, wherein the one or more user commands comprise at least one of:
setting a start point of the multimedia data;
setting an end point of the multimedia data;
removing background from the multimedia data;
assigning one or more tags to the multimedia data; and
sharing the multimedia data with a set of other users.

19. The smart mirror of claim 14, wherein the processor instructions, on execution, further cause the processor to:
receive multimedia data from the activity expert corresponding to the target activity performance in real-time in response to the current activity performance of the user; and
display the set of user performance parameters and the target activity performance of the activity expert in real-time through the GUI via the smart mirror, wherein the target activity performance is overlaid over the reflection of the current activity performance of the user in real-time.

20. The smart mirror of claim 14, wherein the processor instructions, on execution, further cause the processor to:
detect, via the at least one camera, an initial position of the user;
determine whether the detected initial position of the user matches an initial position mapped to the activity from the plurality of activities; and
instruct the user to correct the initial position, when the detected initial position fails to match the initial position.

* * * * *